(12) United States Patent
Schlicker et al.

(10) Patent No.: US 7,289,913 B2
(45) Date of Patent: Oct. 30, 2007

(54) LOCAL FEATURE CHARACTERIZATION USING QUASISTATIC ELECTROMAGNETIC SENSORS

(75) Inventors: Darrell E. Schlicker, Watertown, MA (US); Neil J. Goldfine, Newton, MA (US); Andrew P. Washabaugh, Chula Vista, CA (US); Yanko K. Sheiretov, Waltham, MA (US); Mark D. Windoloski, Chelmsford, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 0 days.

(21) Appl. No.: 11/249,047

(22) Filed: Oct. 11, 2005

(65) Prior Publication Data

US 2006/0097718 A1    May 11, 2006

Related U.S. Application Data

(60) Provisional application No. 60/616,963, filed on Oct. 8, 2004.

(51) Int. Cl.
*G01B 7/34* (2006.01)
*G06F 17/40* (2006.01)
*G06F 19/00* (2006.01)

(52) U.S. Cl. .................. 702/38; 73/865.8; 73/866; 324/200; 324/222; 324/228; 324/234; 324/238; 702/35; 702/36

(58) Field of Classification Search .............. 73/865.8, 73/866; 324/200, 222, 228, 234, 236, 237, 324/238; 702/33, 35, 36, 38, 57
See application file for complete search history.

(56) References Cited

U.S. PATENT DOCUMENTS 4,763,070 A * 8/1988 Huschelrath ................ 324/225
4,814,690 A    3/1989 Melcher et al.

(Continued)

FOREIGN PATENT DOCUMENTS

GB    2082330 A *   3/1982

OTHER PUBLICATIONS

Navy Phase II Final Report, titled "*Three Dimensional Magnetic Imaging of Damage in Multiple Layer Aircraft Structures*" Topic #N02-28144, dated Aug. 1, 2005.

(Continued)

*Primary Examiner*—Edward R Cosimano
(74) *Attorney, Agent, or Firm*—Hamilton Brook Smith & Reynolds, P.C.

(57) ABSTRACT

Local features such as cracks in materials are nondestructively characterized by measuring a response with an electromagnetic sensor and converting this response into a selected property using a database. The database is generated prior to data acquisition by using a model to generate a baseline response or field distribution for the sensor and combining these results with another model, which may be simpler than the first model or provide a local representation of the field perturbations around a feature, which is evaluated multiple times over a range of values of the selected property. In addition, the presence of a feature may be detected by converting the sensor response into a reference parameter, such as a lift-off factor that reflects the sensor position relative to a material edge, and using this parameter to determine a reference response that can be compared to the measured response.

14 Claims, 16 Drawing Sheets

U.S. PATENT DOCUMENTS

| | | |
|---|---|---|
| 5,015,951 A | 5/1991 | Melcher |
| 5,453,689 A | 9/1995 | Goldfine et al. |
| 5,793,206 A | 8/1998 | Goldfine et al. |
| RE36,986 E | 12/2000 | Melcher |
| 6,188,218 B1 | 2/2001 | Goldfine et al. |
| 6,249,755 B1 * | 6/2001 | Yemini et al. .............. 702/183 |
| 6,380,747 B1 | 4/2002 | Goldfine et al. |
| 6,486,673 B1 | 11/2002 | Goldfine et al. |
| 6,566,871 B2 * | 5/2003 | Holzl ........................ 324/240 |
| 6,657,429 B1 | 12/2003 | Goldfine et al. |
| 6,781,387 B2 | 8/2004 | Goldfine et al. |
| 6,784,662 B2 | 8/2004 | Schlicker et al. |
| 6,920,596 B2 * | 7/2005 | Sagatelian et al. .......... 714/732 |
| 6,952,095 B1 | 10/2005 | Goldfine et al. |
| 7,003,433 B2 * | 2/2006 | Yemini et al. .............. 702/183 |
| 7,075,315 B2 * | 7/2006 | Tanaka ....................... 324/642 |
| 7,107,185 B1 * | 9/2006 | Yemini et al. .............. 702/183 |
| 2002/0074996 A1 * | 6/2002 | Holzl ........................ 324/240 |
| 2002/0075006 A1 | 6/2002 | Goldfine et al. |
| 2002/0158626 A1 | 10/2002 | Shay et al. |
| 2003/0098697 A1 * | 5/2003 | Tanaka ....................... 324/637 |
| 2003/0140294 A1 * | 7/2003 | Sagatelian et al. .......... 714/732 |
| 2003/0164700 A1 | 9/2003 | Goldfine et al. |
| 2004/0056654 A1 | 3/2004 | Goldfine et al. |
| 2004/0066188 A1 | 4/2004 | Goldfine et al. |
| 2005/0127908 A1 | 6/2005 | Schlicker et al. |
| 2005/0137832 A1 * | 6/2005 | Yemini et al. .............. 702/183 |

OTHER PUBLICATIONS

Strang G., *Introduction to Applied Mathematics*. Chapter 5, pp. 367-470, Wellesley-Cambridge Press, Wellesley, Massachusetts, 1986.

* cited by examiner

LOCAL FEATURE CHARACTERIZATION USING QUASISTATIC ELECTROMAGNETIC SENSORS

RELATED APPLICATION(S)

This application claims the benefit of now expired U.S. Provisional Application No. 60/616,963 filed Oct. 8, 2004, the entire teachings of which are incorporated herein by reference.

BACKGROUND OF THE INVENTION

The technical field of this invention is that of nondestructive materials characterization, particularly quantitative, model-based characterization of surface, near-surface, and bulk material condition for flat and curved parts or components. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing the material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution. Spatially periodic field eddy-current sensors have been used to measure foil thickness, characterize coatings, and measure porosity, as well as to measure property profiles as a function of depth into a part, as disclosed in U.S. Pat. Nos. 5,015,951 and 5,453,689.

Common methods for measuring the material properties use interrogating fields, such as electric, magnetic, thermal or acoustic fields. The type of field to be used depends upon the nominal properties of the test material and the condition of interest, such as the depth and location of any features or defects. For relatively complicated heterogeneous materials, such as layered media, each layer typically has different properties so that multiple methods are used to characterize the entire material. However, when successively applying each method, there is no guarantee that each sensor is placed at the same distance to the surface or that the same material region is being tested with each method without careful registration of each sensor.

A common inspection technique, termed conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks. A particular difficulty with eddy current sensors is the effect of material discontinuities, such as edges of the material. These edges can strongly influence the response of the sensor and potentially mask the response of cracks that commonly form at these edges.

SUMMARY OF THE INVENTION

Aspects of the methods described herein involve nondestructive evaluation of materials for the detection and characterization of local features or condition monitoring. The local features, such as cracks, are represented with notch-like features and may occur at the edges of the test material. Responses measured with a sensor are converted into effective properties, such as the length or depth of a feature or the temperature on a hidden surface by using a precomputed database of responses generated prior to data acquisition with a combination of models.

In one embodiment, a database for measuring a selected property of a local feature involves first defining the physical and geometric properties of the test material and sensor. This includes defining at least one selected property that is to be determined by measurement with sensor and a range of values for each property. The operating point parameters, such as the excitation frequency, temperature, and other environmental conditions are also defined. These values are then input to a model that neglects the presence of the local feature to determine a baseline interrogation field distribution that would be associated with the sensor. The field distribution is then input to a local model representation for the change in the field due to the presence of the local feature. The change in field values affects the input/output terminal value for the sensor, which are then stored in a database. This database can then be used with sensor measurements to determine a selected property of the evaluating a test material. In embodiments, the local feature is a notch or a crack, with a selected property the depth, length, position of the feature position relative to the sensor, sensor proximity to the test material surface, or a parameter that represents the time-varying evolutions of the feature, such as crack length as a function of the number of load cycles.

In an embodiment, a method for generating a database of sensor responses for measuring a selected property of a local feature is performed. The steps comprises of defining properties of a test material, a sensor, and the local feature in the test material. A model incorporating properties for the sensor and the material without the local feature is analyzed in order to compute an interrogation field. The computed interrogation field is inputted into a local model representing change in field in the vicinity of the feature to compute input/output terminal relation values for the sensor response for multiple values of the selected property of the local feature, and recording the terminal relation values in a database.

In an embodiment, the baseline response is obtained for a material having a complex geometry, such as a material edge, a fastener hole, or a fastener. The interrogating field for this baseline response can be determined by computationally relatively slow generic numerical methods, such as finite element or boundary element techniques. Alternatively, for a layered material geometry quasi-analytical methods can be used. In another embodiment, the geometric properties for the sensor account for a width and thickness of the conducting electrodes or windings. In an embodiment, the dominant interrogating field is an electric or a magnetic field. For an imposed magnetic field, an embodiment of the local model involves providing a parametric description of the charge on the local feature surface and in the vicinity of the feature. The surface charge is then determined from interfacial electromagnetic boundary conditions and used to calculate, in turn, the change in induced electric current caused by the presence of the feature, the change in the total magnetic field, and the sensor response.

In another embodiment, a property of a material having a complex geometry is obtained measuring a response from a sensor disposed proximate to a test material and converting the response into the property using a database of precomputed responses. The database is generated from a computational model that accounts for the complex geometry of the material, such as a material edge or the presence of a fastener, along with a simplified model that can provide a relation between the sensor response and the perturbations in the property of interest. In embodiments, the property of interest is the temperature on a hidden surface of the stress on a material.

In yet another embodiment, cracks or local features in a test material are detected by measuring a response from a sensor disposed proximate to a test material and converting the response into a reference parameter. This reference parameter is then used to obtain a reference response that can be compared to the measured response to determine if a local feature is present. The reference response can be obtained from a database of reference responses that are determined empirically or from models. In an embodiment, the sensor is placed near a material edge and the sense element response is measured at multiple positions along the edge. In another embodiment, the response is converted into a lift-off value and an effective material property, such as an electrical conductivity. In an embodiment, the reference parameter is the lift-off. In another embodiment, when the sensor is near a material edge, the reference parameter represents the sense element position over the edge. As a specific example, this reference parameter is a linear function of the lift-off.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 24 shows a representative data for a sensor array scanned along an edge with an offset of 0.0 in.

FIG. 25 shows a representative data for a sensor array scanned along an edge with an offset of 0.01 in.

FIG. 26 shows a representative data for a sensor array scanned along an edge with an offset of 0.02 in.

FIG. 27 shows a representative data for a sensor array scanned along an edge with an offset of 0.03 in.

FIG. 28 shows a representative data for a sensor array scanned along an edge with an offset of 0.04 in.

FIG. 29 shows a representative data for a sensor array scanned along an edge with an offset of 0.05 in.

DETAILED DESCRIPTION OF THE INVENTION

Figure 1:
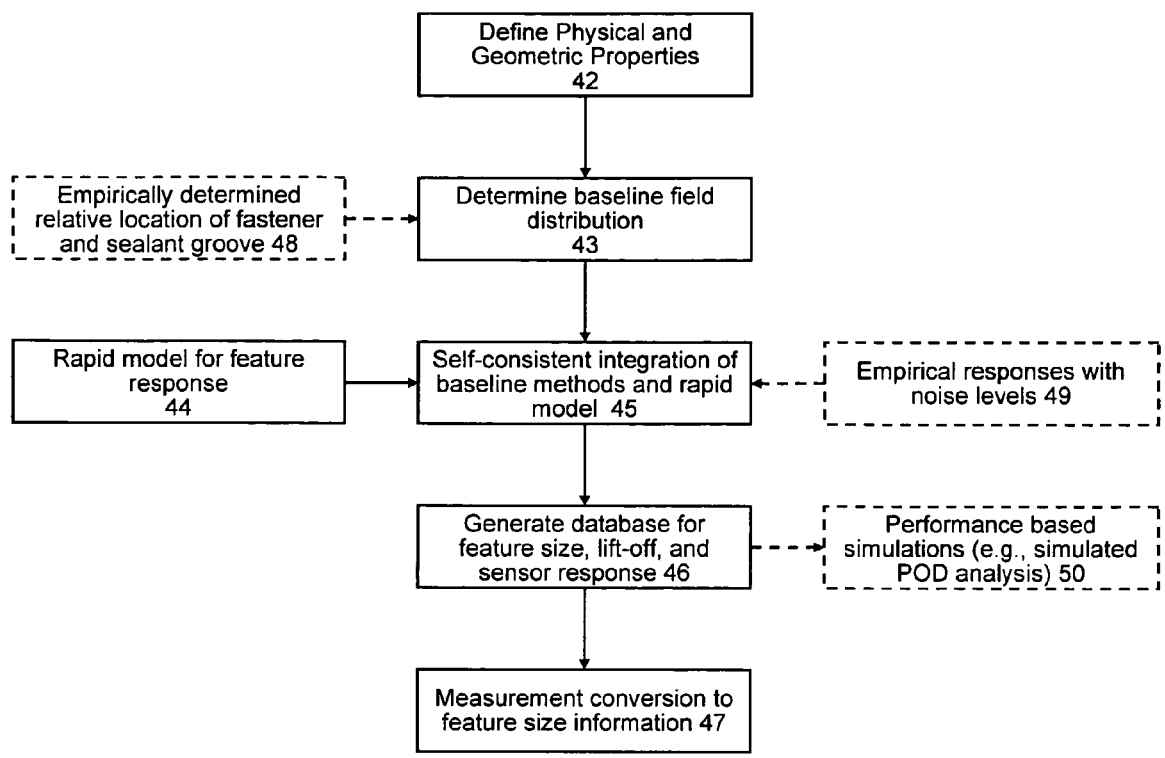
FIG. 1 illustrates generation of a database of responses combining a relatively slow model to determine a nominal field distribution with a relatively fast model to calculate field changes due to a local feature in a test material.

A description of preferred embodiments of the invention follows.

This invention is directed toward the detection and characterization of notch-like local features, such as cracks, that may even occur at the edges of a test material. The use of models that can rapidly and accurately predict the sensor response allows measured sensor responses to be converted into estimates of effective properties that can characterize the test material and the feature. Some of the effective properties of the test material, such as electrical conductivity, magnetic permeability, dielectric permittivity, and the thicknesses of material layers, such as a lift-off or sensor proximity, can be used to correct for sensor resporises near material edges or even select appropriate reference scans for filtering sensor responses. Other effective properties can represent the length, width, depth, or shape of the feature.

One of the limiting factors in establishing the response of a sensor to a notch-like feature such as a crack is the computation time required for solving the field distribution. The most accurate approach in estimating the sensor response is to solve for the electromagnetic fields in the total system composed of the sensor and the material under test (MUT) containing the notch. However, since accurate closed form solutions are not available for simplistic cases of a sensor in the presence of a uniform material, the introduction of a notch does not allow for this type of closed form solution either. Indeed, the introduction of the notch converts the two-dimensional problem of the sensor and MUT into a three-dimensional one. The conventional approach for solving this type of problem is the use of three dimensional finite element (FE) or boundary element (BE) methods, which solve Maxwell's Equations by filling the volume or surfaces of the problem with basis functions having local support (reference Strang, 1986). These functions contain unknown coefficients that must then be solved according to the governing differential equations, boundary conditions, and terminal constraints. Generally, the number of unknowns increases dramatically with the model volume in FE methods or model surface areas in BE methods. Then, introducing a feature such as a notch or a crack into the test material can take excessively long to accurately compute the sensor response, either as a scan over the material surface or for different notch sizes. In comparison, methods outlined in pending U.S. patent application Ser. No. 10/963,482 filed on Oct. 12, 2004, which published as U.S. Patent Application Publication No. 2005/0127908, the entire teachings of which are incorporated herein by reference, only introduced unknown parameters along a line and provide accurate field solutions and sensor response for layered media. For a local feature or a notch, the perturbation in an imposed field is determined and the numerical discretization is only in the vicinity of the notch. This approach then allows for rapid determinations of the sensor response to a notch since only the perturbation field in the vicinity of the notch needs to be determined as the sensor position is varied.

FIG. 1 shows an outline for this approach as applied to the generation of a database of sensor responses. First, the physical and geometric properties for both the test material and sensor 42 are defined. This definition may also involve defining the properties of complex geometries for the material such as material edges, holes, burnishing grooves, or fasteners. This also involves defining a range of values of interest for a selected property that is eventually to be determined with measurements using this database. This also includes defining operating point parameters, such as the excitation frequency for the sensor. This information is then used to calculate the nominal field distribution using a relatively slow numerical method, such as finite element or boundary element methods 43. Conventional modeling software, commonly based on finite element or boundary element methods, which are relatively slow and memory intensive, would be run relatively infrequently in order to get the nominal electromagnetic field distribution. The nominal field distribution information is then combined 45 with a computationally rapid model for the response of a local feature 44 in the test material to determine the terminal values and changes in these terminal values for the sensor response due to the presence of the local feature. The rapid model is run repeatedly to populate the response database 46 (grid, lattice or hypercube, as necessary). These databases are used to convert the sensor information into local feature size information 47, such as crack length or depth information. Empirical information obtained from measurements on the part itself can be used to determine the relative location of the fastener in the sealant groove 48. In addition, empirical information about the instrument or measurement noise levels 49 can be used when integrating the rapid and element-based models together to determine, for example, the appropriate measurement frequencies. The precomputed databases relating the sensor response to crack size, depth, and location, lift-off, and sealant groove position can be used both for inversion of the measured responses to estimate crack size estimates as well as to provide performance based simulations such as simulated probability of detection (POD) curve generation 50. The models used in calculating the sensor responses may also represent other behavior of the material, such as the time-varying damage state evolution of a crack.

Figure 2:
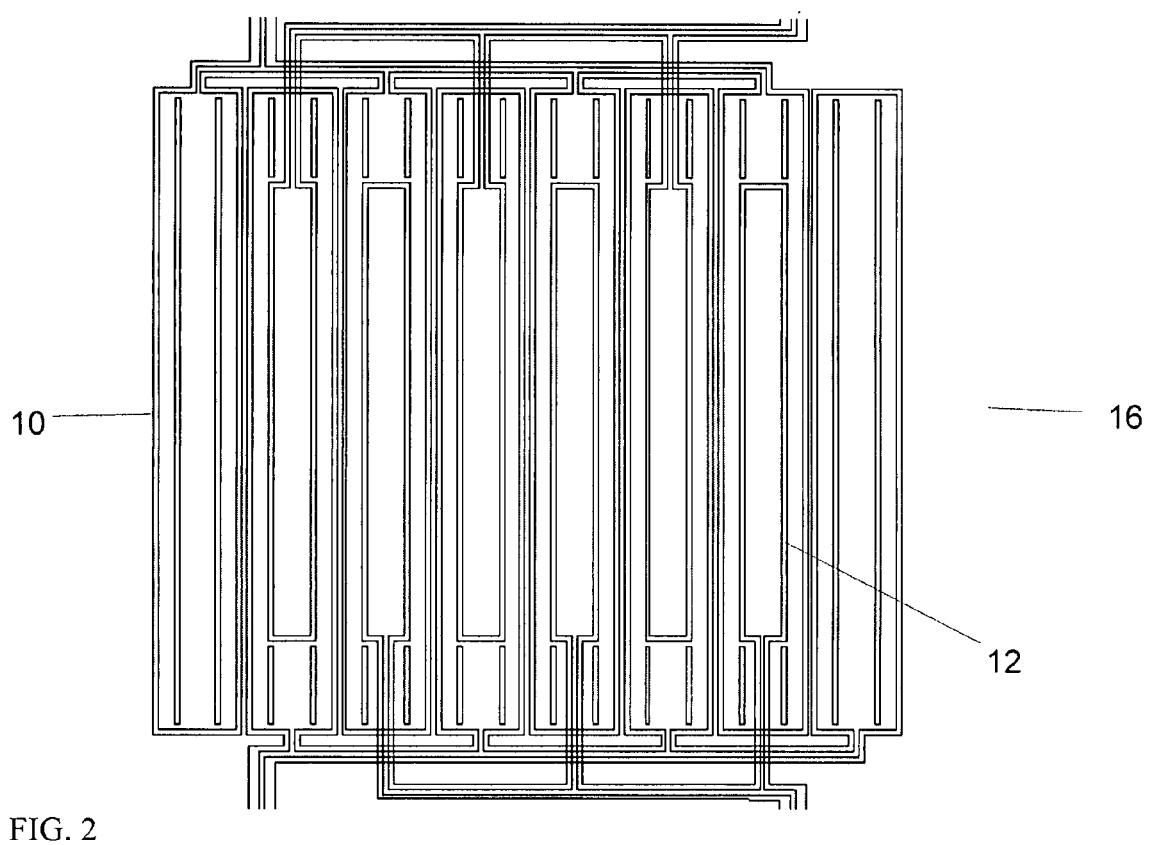
FIG. 2 shows a drawing of a spatially periodic field eddy-current sensor.

An example magnetic field based sensor that operates in the magnetoquasistatic regime and is well-suited to this approach is shown in FIG. 2. This meandering winding magnetometer (MWM®) is a "planar," conformable eddy-current sensor that was designed to support quantitative and autonomous data interpretation methods. The sensor 16 is described in U.S. Pat. Nos. 5,453,689, 5,793,206, 6,188,218, 6,657,429 and U.S. patent application Ser. No. 09/666,524 filed on Sep. 20, 2000, now U.S. Pat. No. 6,952,095, and U.S. patent application Ser. No. 10/633,905 filed Aug. 4, 2003, which published as U.S. Patent Application Publication No. 2004/0066188, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength $\lambda$. A current is applied to the primary winding to create a magnetic field and the response of the MUT to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. No. 5,793,206 and Re. 36,986.

The MWM-Arrays typically have one or more drive windings, possibly a single rectangle, and multiple sensing elements for inspecting the test material. Some of the motivation for the use of multiple sensing elements is to increase the spatial resolution of the material being characterized without loss of coverage, to add additional information for use in the estimation of multiple unknown material properties, and to cover large inspection areas in a faster time. These arrays can be used in both permanently mounted or scanning applications.

Figure 3:
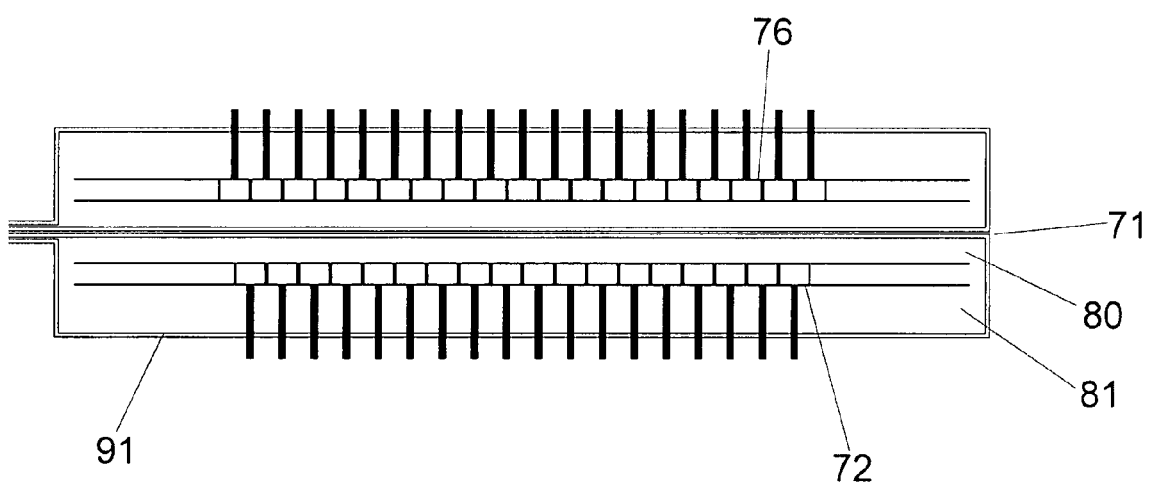
FIG. 3 shows a plan view of sensor array with a single primary winding and an array of sensing elements with connections to each individual element.
Figure 4:
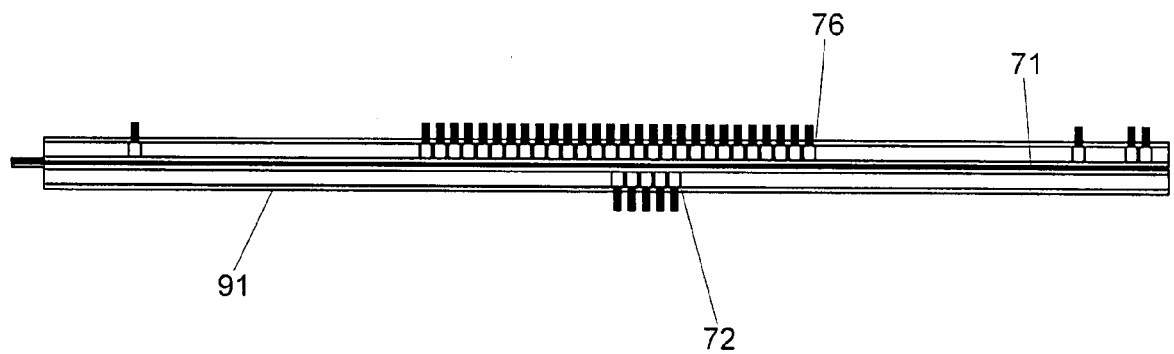
FIG. 4 is an expanded view of an eddy-current array where the locations of the sensing elements along the array are staggered.

The dimensions for the sensor array geometry and the placement of the sensing elements can be adjusted to improve sensitivity for a specific inspection. For example, the effective spatial wavelength or four times the distance 80 between the central conductors 71 and the sensing elements 72 can be altered to adjust the sensitivity of a measurement for a particular inspection. For the sensor array of FIG. 3, the distance 80 between the secondary elements 72 and the central conductors 71 is smaller than the distance 81 between the sensing elements 72 and the return conductor 91. An optimum response can be determined with models, empirically, or with some combination of the two. An example of a modified design is shown in FIG. 4. Here, most of the sensing elements 76 are located in a single row to provide the basic image of the material properties. A small number of sensing elements 72 are offset from this row to create a higher image resolution in a specific location.

Figure 5:
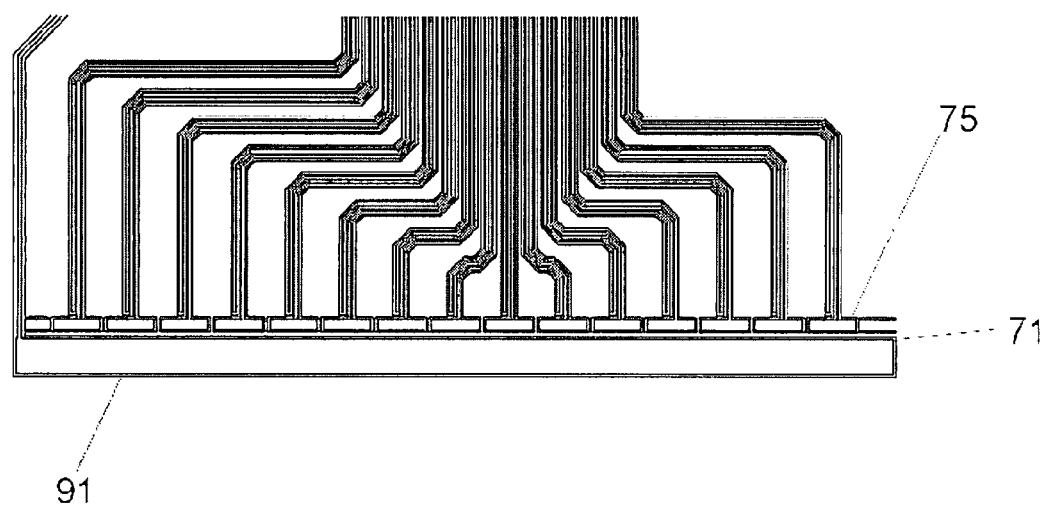
FIG. 5 is an expanded view of an eddy current array with a single rectangular loop drive winding and a linear row of sense elements on the outside of the extended portion of the loop.

The number of conductors used in the primary winding can be reduced further so that a single rectangular drive is used. As shown in FIG. 5, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. This distance can be optimized using models to maximize sensitivity to a feature of interest such as a buried crack or stress at a specific depth. Advantages of the design in FIG. 5 include a narrow drive and sense structure that allows measurements close to material edges and non-crossing conductor pathways so that a single layer design can be used with all of the conductors in the sensing region in the same plane. The width of the conductor 91 farthest from the sensing elements can be made wider in order to reduce any ohmic heating from large currents being driven through the drive winding.

An efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grid" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for near real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 6:
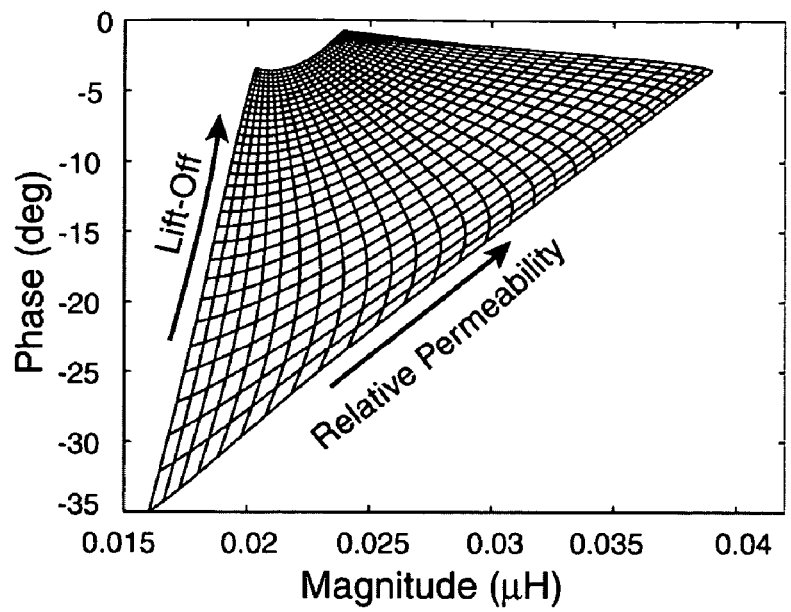
FIG. 6 shows a representative measurement grid relating the magnitude and phase of the sensor terminal impedance to the lift-off and magnetic permeability.
Figure 7:
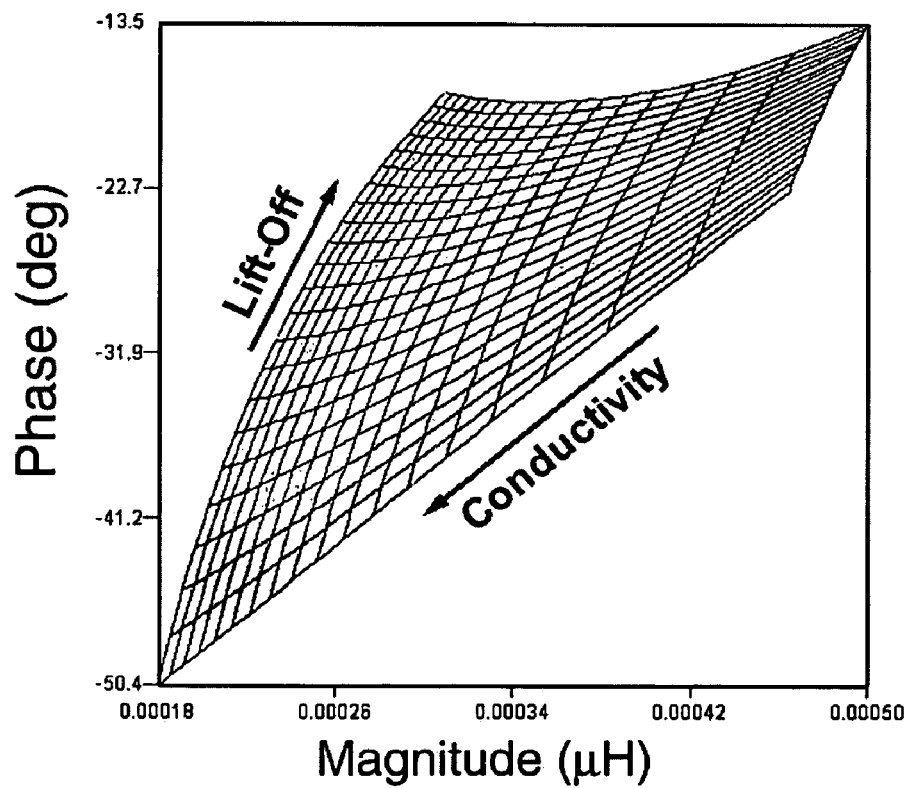
FIG. 7 shows a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 6. A representative measurement grid for a low-conductivity nonmagnetic alloy (e.g., titanium alloys, some superalloys, and austenitic stainless steels) is illustrated in FIG. 7. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses. The effective property can also be a layer thickness, which is particularly suitable for coated systems. The effective property could also be some other estimated damage state, such as the dimension of a flaw or some indication of thermal damage for the material condition.

In addition to inductive coils, other types of sensing elements, such as Hall effect sensors, magnetoresistive sensors, SQUIDS, Barkhausen noise sensors, and giant magnetoresistive (GMR) devices, can also be used for the measurements. The use of GMR sensors for characterization of materials is described in more detail in U.S. patent application Ser. No. 10/045,650, filed Nov. 8, 2001, now U.S. Pat. No. 6,992,482, the entire teachings of which are incorporated herein by reference. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations.

For insulating or weakly conducting materials such as fiberglass composites, capacitive or dielectric sensors can be used. The sensors are the electromagnetic dual to the inductive sensors, with electric fields taking the place of magnetic fields for inspecting the materials and can be used to monitor stress or temperature, moisture content or contamination or overload of fatigue in adhesives, epoxies, glass, oil, plastics and in single or multiple layered media. Here the conductivity and dielectric constant or complex permittivity and layer thicknesses are measured using the same methods as for magnetic field sensing, except that the sensors operate in the electroquasistatic regime. In one such electric field method multiple layers of material are added to a base material with each layer sensitive to different chemicals or biological materials. These different layers may be sensitive to contaminants, biological agents, reagents, or chemical threats and can provide a change in dielectric properties to any of these other materials. By exposing such selective or sensitive material layers to a test environment, such as a gas, liquid, or fluid, the property change in the material layer can be monitored and use to assess the presence of unhealthy cells, particulate matter, or other agents. The sensitivity of the material layer may also be altered by adding other reagents.

Figure 8:
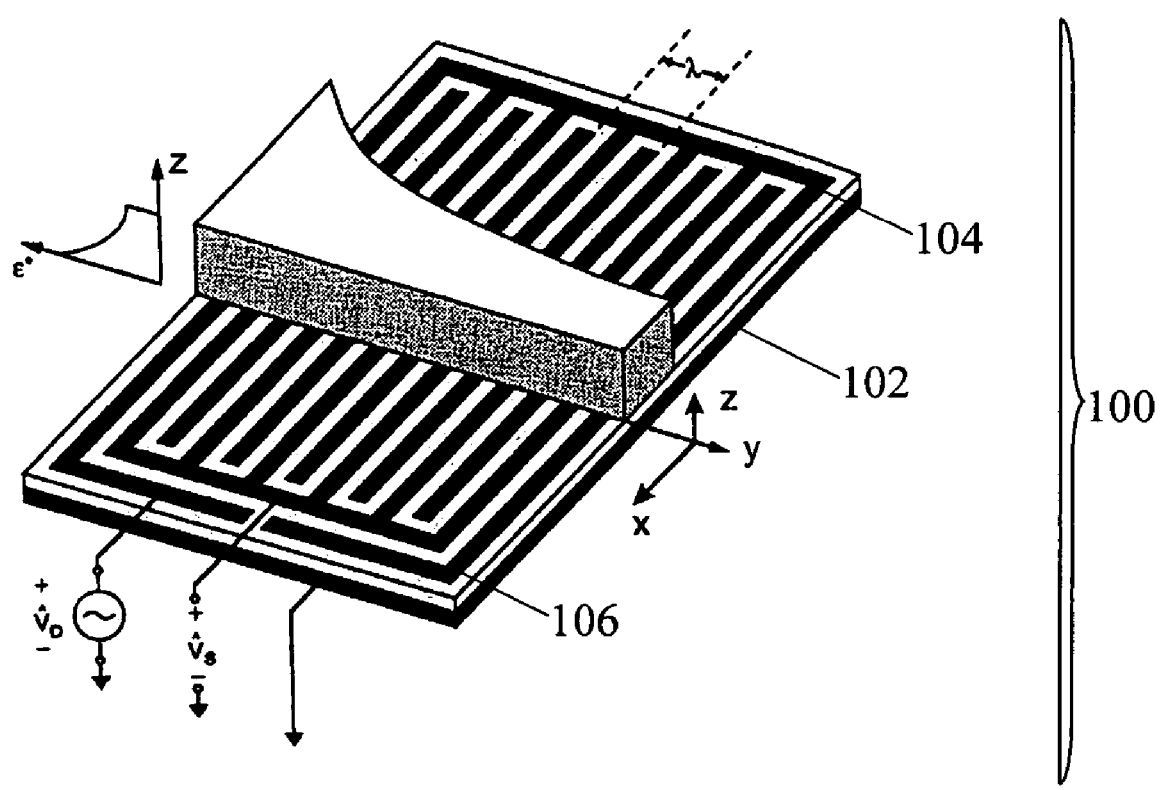
FIG. 8 shows a representative single wavelength interdigitated electrode dielectrometer with spatially periodic driven and sensing electrodes that can measure dielectric properties of the adjacent material

A representative single sided sensor geometry is shown in FIG. 8. The application of a sinusoidally time varying potential of angular frequency $\omega=2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, 6,486,673 and 6,781,387 and in now abandoned U.S. patent application Ser. No. 10/040,797, filed Jan. 7, 2002, which published as U.S. Patent Application Publication 2002/0075006, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_S$ or to a virtually grounded amplifier to measure the magnitude and phase of the terminal current I. The periodicity of the electrode structure is denoted by the spatial wavelength $\lambda=2\pi/k$, where k is the wavenumber.

Figure 9:
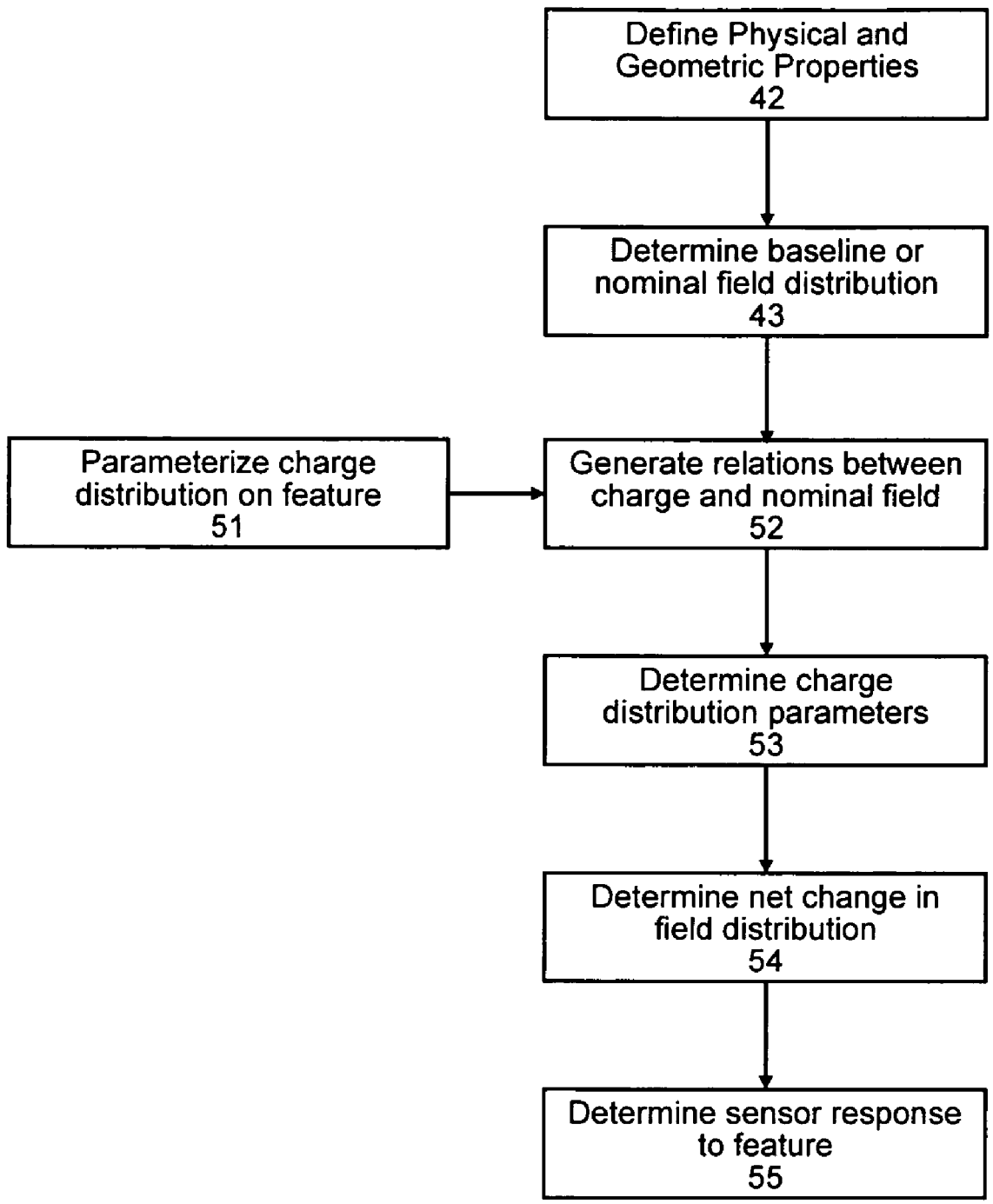
FIG. 9 illustrates the application of a rapid local model with a nominal field distribution to determine a sensor response.

FIG. 9 shows a schematic outline of the relatively fast local model for calculating the changes or perturbations in the field distribution and sensor response for an electromagnetic sensor. As in FIG. 1, the first steps involve defining the physical and geometric properties 42 for the test material and sensor and using this information to determine the nominal interrogation field distribution 43. For a magnetic field sensor, a time-varying interrogating magnetic field induces eddy currents in the test material, whose flow is perturbed by the presence of local features such as cracks or notches. The rapid local model determines these changes in the local fields by parameterizing the charge distribution on the material surfaces near the feature and the feature itself 51. These parameterized charge distributions are then related to the nominal field distribution 52 using interfacial boundary conditions and used to determine the charge distribution parameters 53. This allows the net change in the field distribution (both induced eddy current and total magnetic field) to be determined 54, along with the sensor response to the feature 55. This process is readily repeated for different feature sizes, such as length and depth, or position relative to the sensor once the nominal field distribution is determined. The following provides a more detail description of the local feature model for a magnetic field sensor In this example, the model is applied to notches having a simple rectangular box shape oriented such that the faces are either parallel or perpendicular to the MUT surface to which the sensor is parallel. The material within the notch is assumed to have the properties of free space. The notch is located in one of three possible locations: surface breaking at the surface near the sensor, buried inside the MUT surfaces, or surface breaking at a MUT surface opposite the MUT surface near the sensor. For the first two cases the material may be infinitely thick, in which case only the single surface near the sensor is considered.

With the unperturbed field and currents in the MUT determined by other methods, the perturbing affect of the notch on the sensor's terminal response is to be considered. The response of the notch as detected by the sensor is due to the notch's alteration of the currents flowing in the material and therefore the magnetic flux coupled at the sensor's secondary sensing elements. The fact that the notch is nonconducting requires that no currents flow within the volume of the notch and therefore the coupling to the sensing elements by the magnetic fields produced by these currents must be subtracted. It is being assumed that the direct perturbing effect caused by the absence of these currents on the fields and currents within the volume outside of the notch will be negligible, such that at this part of the analysis the external fields and currents are assumed equivalent to those of the unperturbed system. Since the current density within the notch is treated as zero, the current density at the surface of the notch is no longer continuous and therefore conservation of charge at the surface requires:

$$\vec{n} \cdot \|\vec{J}\| = -\frac{\partial \rho_{fs}}{\partial t} \qquad (1)$$

where $\vec{n}$ is the surface normal, $\|\vec{J}\|$ is the jump in the volume current density across the surface, and $\rho_{fs}$ is the free surface charge density. The current density in the notch is zero and conduction in the MUT is ohmic, characterized by conductivity $\sigma_M$. The system is excited by a sinusoidal excitation and therefore (1) can be simplified to the time-harmonic form:

$$\vec{n} \cdot \sigma_M \vec{E}_s = -j\omega \hat{\rho}_{fs} \qquad (2)$$

where $\vec{n}$ is now the normal of a surface pointing into the conducting region, and $\overline{E}_s$ is the electric field on the conducting side of the interface.

Charge must accumulate on the surfaces of the notch such that this equation of charge conservation is obeyed. Since the system is composed of highly conducting metals and free space, only free charge will be significant (i.e., polarization charge need not be considered such that $\epsilon=\epsilon_0$). The accumulated surface charge will produce an electric field which must be superimposed on the unperturbed field in enforcing (2). The MUT is assumed to have homogenous electrical properties which does not allow for volume charge accumulation to result from the perturbation field. However, the field caused by the surface charge on the notch will generally have components normal to the other MUT surfaces. In order for charge conservation to be obeyed at these surfaces, surface charge contributing to the perturbation electric field must be allowed on these surfaces also.

If the surface charge can be evaluated such that charge conservation boundary conditions can be met then the perturbation of the volume currents can also be obtained from the charge distribution. The magnetic fields created by these perturbation currents and coupled to the sensing elements can then be added to the total sensor response.

An assumption has been made here that the total electric field is simply the initial field superimposed with the field from charge sources. However, an exact solution would also account for contribution to the electric field made by the perturbation magnetic fields. Of course a complete solution would simultaneously handle the coupling of electric and magnetic fields and not necessarily approach it as an iterative perturbation. Accounting for the coupling of electric and magnetic fields is equivalent to including magnetic diffusion effects in the notch's perturbation of the initial fields. By making these simplifying assumptions, the unknowns which must be determined are reduced from vector quantities over the complete volume in a FEM approach to the scalar surface charge density quantities over a limited surface area.

The modeling method is summarized in the following steps: (1) Allow for surface charge distributions on notch and MUT surfaces in terms of unknown parameters. (2) Determine total electric field at surfaces in terms of initial electric field and perturbation electric fields from accumulated charge. (3) Impose charge conservation at surface boundaries and solve for charge distribution parameters. (4) Use charge distribution parameters to evaluate perturbation electric fields and thereby perturbation currents in the volume of the MUT surrounding the notch. (5) Calculate the magnetic flux produced by perturbation currents and coupled to sensing elements. (6) Add perturbation in sensing element terminal voltage resulting from coupled magnetic flux to total sensing element terminal voltage as calculated using layered models. (7) Subtract perturbation in sensing element terminal voltage resulting from the absence of layered model currents within the volume of the notch.

As mentioned in the preceding steps, the surface charge density on the surfaces of the notch and the MUT needs to be defined in terms of unknown parameters. Due to the rectangular geometries involved (i.e., rectangular notch faces and perimeter of notch on the MUT surfaces), a bilinear interpolation method is applied in which the charge density within a rectangular region can be determined in terms of the corner values. The charge within these rectangular cells is described by:

$$\hat{\rho}_{fs}(x, y) = \hat{\rho}_{fs}(0, 0)\frac{(x - \Delta_x)(y - \Delta_y)}{\Delta_x \Delta_y} - \quad (3)$$

$$\hat{\rho}_{fs}(\Delta_x, 0)\frac{x(y - \Delta_y)}{\Delta_x \Delta_y} - \hat{\rho}_{fs}(0, \Delta_y)\frac{(x - \Delta_x)y}{\Delta_x \Delta_y} + \hat{\rho}_{fs}(\Delta_x, \Delta_y)\frac{xy}{\Delta_x \Delta_y}$$

where the coordinates x and y represent position within the plane of the surface for a rectangular region with a corner at the origin and an opposite corner located at ($\Delta_x$, $\Delta_y$).

Larger rectangular surfaces regions can be formed by locating equally sized bilinear regions on a regular grid (with grid spacing-equivalent to cell dimensions), such that adjacent edges of the smaller bilinear regions share corner points. The result is a surface region with a surface charge density that is continuous. This method is sufficient to cover the surfaces involved, which include the faces of the notch that border the conductive MUT and a rectangular perimeter around the notch on the MUT surfaces. Surface breaking notches are handled by choosing an appropriate cell size for the MUT surface such that the cells on the surface breaking face of the notch can be omitted in a way that allows the immediate perimeter of the notch face to remain completely covered by cells. The MUT surfaces do not require coverage of infinite extent since the surface charge accumulated on these surfaces will decay with distance from the notch to a point where the surface charge density can be assumed as zero with minimal error. It should also be noted that there is no requirement that the surface charge density be continuous at edges of non-coplanar surfaces that intersect, such as along edges of the notch where the faces intersect.

Although it is sufficient to use a single rectangular cell size and a single large rectangular region of cells per surface, it is not optimal in terms of the number of unknowns that will ultimately need to be determined. Therefore it is desired to use multiple rectangular regions of cells, each possibly using a different cell size to cover the required region of a surface. The lack of a requirement that charge be continuous on meeting edges of non-coplanar sides does not apply here since the surface that will contain these multiple larger rectangular regions is indeed coplanar with itself. Moreover, one expects the surface charge on a planar surface to be continuous in the absence of any geometric or electric property discontinuities. This means that the surface charge density along the edge of two larger rectangular regions should be continuous. However, the desire to allow different cell sizes within these rectangular regions will not allow a strict continuity to be achieved. Fortunately no derivatives of the surface charge functions will be taken in calculations, but rather the charge functions will be used in integration (summation) reducing any errors created by a discontinuity.

However, for the purposes of numerical stability, a pseudo-continuity is still required. This becomes an issue when boundary conditions on charge conservation are applied. If the surface charge density at the meeting edges of these rectangular regions are not coupled in some way, boundary conditions imposed along the edge may be met numerically as the result of two large oppositely signed charge density values, one from each region, in the vicinity of the point at which the boundary condition is imposed. This type of behavior would produce non-physical solutions and a poor predicted sensor response.

To impose this pseudo-continuity, one of the meeting edges is designated as the driving edge, typically the one with a large cell size, while the other is designated as the driven edge. Edges of a rectangular region meeting with multiple other rectangular regions may have its edge segmented into driving and driven pieces. The cell corner values from the driven edge are determined in terms of the cell corner values of the driving edge by applying (3).

Figure 10:
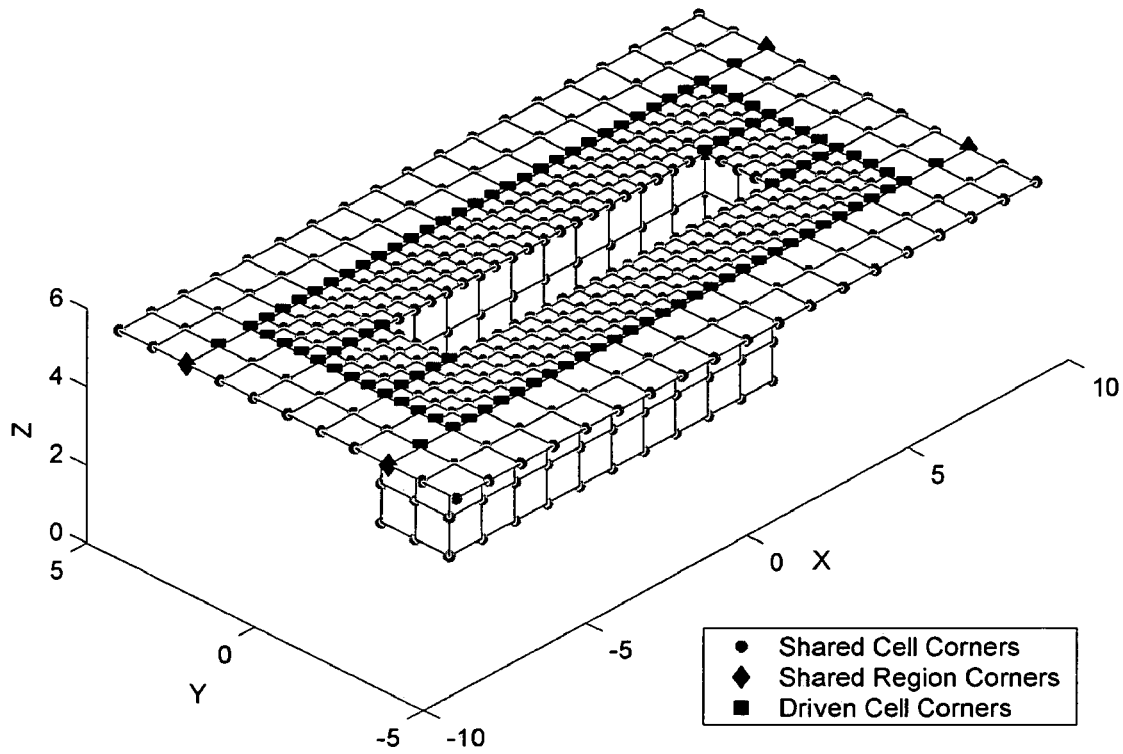
FIG. 10 shows a representation of surface charge density by bilinear interpolation cells.

An example for the location of cells and corner points can be seen in FIG. 10. For the MUT surface on which the notch is surface breaking, eight rectangular regions are used to cover a sufficient perimeter of the surface breaking notch face. A smaller cell size is chosen near the notch, while a large size is utilized away from the notch where the charge density is expected to vary more slowly. In practice, simulations also utilized multiple rectangular regions on notch faces, such that smaller cells could be incorporated near notch edges and corners.

Choosing the optimal size and distribution of cells and rectangular regions is a balance between accuracy and speed. FE and BE methods typically employ methods of evaluating the size and location of errors and refine the mesh to improve accuracy to a specified level. Although these types of methods could be employed, a more simplistic approach of investigating the effects of increasing the number of cells on the terminal response was employed.

The electric field can now be determined as the superposition of the electric field from the non-perturbed problem $\vec{E}_0(\vec{r})$ and the electric field due to the accumulated surface charge $\vec{E}_1(\vec{r})$, such that the total electric field is:

$$\vec{E}_T(\vec{r}) = \vec{E}_0(\vec{r}) + \vec{E}_1(\vec{r}) \qquad (4)$$

where $\vec{r}$ is the position vector within the volume of the problem. The electric field from the accumulated charge can be evaluated using the superposition integral over the volume:

$$\vec{E}_1(\vec{r}) = \frac{1}{4\pi\varepsilon_0} \int_V \frac{\hat{\rho}_{fv}(\vec{r}')}{|\vec{r}-\vec{r}'|^2} \vec{i}_{r'r} dV \qquad (5)$$

where $\hat{\rho}_{fv}(\vec{r}')$ is the volume charge distribution and $\vec{i}_{r'r}$ is a unit vector from the position vector $\vec{r}'$ to the position vector $\vec{r}$. Since all of the accumulated charge must be located on the specified rectangular surface regions in the form of surface charge, (5) can be expressed as:

$$\vec{E}_1(\vec{r}) = \frac{1}{4\pi\varepsilon_0} \sum_{regions} \sum_{cells} \int_S \frac{\rho_{fs}(\vec{r}')}{|\vec{r}-\vec{r}'|^2} \vec{i}_{r'r} dS \qquad (6)$$

Equation (3) provides an expression for the surface charge within each cell in terms of the four corner charge density values. One approach is to carry out the integration of (6) after substituting the surface charge expression. Since the charge density values at the corners are constants with position, this would result in an expression for $\vec{E}_1(\vec{r})$ that is linear in terms of these corner values. However, the analytic expression for this integration is rather complex and therefore a numerical approach to evaluating (6) is pursued.

A numerical approach may seem less attractive with the possibility of an analytic expression, but in this case the numerical integration may generally be performed rapidly. This is due to the specifics of the charge distribution $\hat{\rho}_{fs}(\vec{r}')$ within a cell having less of an impact on the integral than the total charge contained within the cell, as the distance from the cell to the point where the electric field is being evaluated is increased. Therefore when $|\vec{r}-\vec{r}'|$ is sufficiently large, all of the charge within the cell can be located at a single point and the simple expression for the field from a point charge can be employed. The total charge within the cell is easily evaluated, due to the bilinear interpolation scheme used, as:

$$\hat{q}_c = \frac{\Delta_x \Delta_y}{4}(\hat{\rho}_{c,1} + \hat{\rho}_{c,2} + \hat{\rho}_{c,3} + \hat{\rho}_{c,4}) \qquad (7)$$

where c is the index of the cell within a specific region and $\hat{\rho}_{c,1}$ through $\hat{\rho}_{c,4}$ are the surface charge density values at its four corners. For terms in the summation of (6) in which $|\vec{r}-\vec{r}'|$ is not large enough to obtain a sufficiently accurate approximation of the integral, some additional work must be done.

Figure 11:
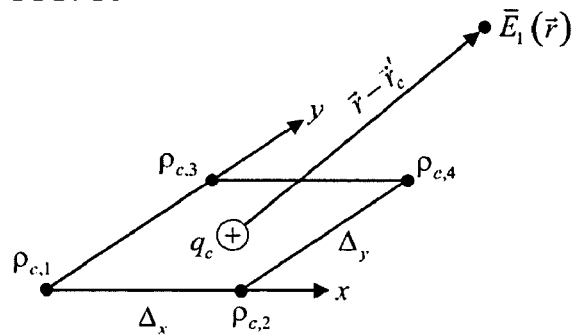
FIG. 11 shows a representation of cell surface charge as a single point charge equal to the net charge within the cell for cases where $|\vec{r} - \vec{r}'_c|$ is sufficiently large.
Figure 12:
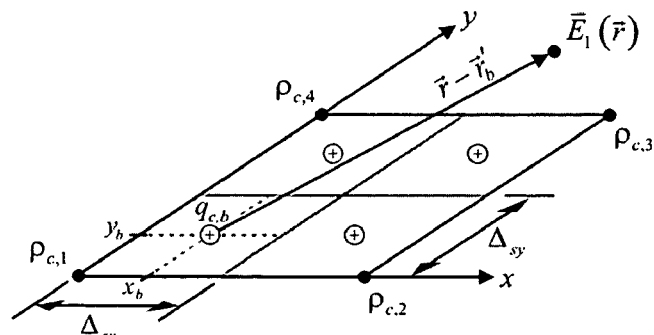
FIG. 12 shows a division of cell into multiple sub-cells, each containing point charges equal to the net surface charge within the corresponding sub-cell, in order maintain an accurate calculation of the perturbation electric fields when $|\vec{r} - \vec{r}'_c|$ is not sufficiently large.

By breaking these cells down into sufficiently small sub-cells, it is generally possible to make the electric field at $\vec{r}$ dependent only on net charge in the sub-cell and not on its specific distribution. In this case the electric field contribution from the charge within a cell can be determined as the summation over the sub-cells by again using the expression for a point charge. The net charge in the sub-cells is then determined from the bilinear interpolation expression for the charge density within the cell and the sub-cell dimensions as:

$$\hat{q}_{c,b} = \Delta_{sx}\Delta_{sy}\hat{\rho}_{sf}(x_b,y_b) \qquad (8)$$

where $\Delta_{sx}$ and $\Delta_{sy}$ are the dimensions of the subcell, $x_b$, $y_b$ is the surface coordinate of the center of the subcell within the cell, and b is the index of the sub-cell within the cell. It should be noted that since the charge within each sub-cell is determined from the interpolation equation, no new unknowns are introduced by this subdivision of the cell. The perturbation electric field resulting from the accumulated surface charge can now be expressed as:

$$\vec{E}_1(\vec{r}) = \frac{1}{4\pi\varepsilon_0} \sum_{regions} \sum_{c}^{cells} \begin{cases} \frac{\Delta_x\Delta_y}{4}\frac{(\hat{\rho}_{c,1}+\hat{\rho}_{c,2}+\hat{\rho}_{c,3}+\hat{\rho}_{c,4})}{|\vec{r}-\vec{r}_c'|^2}\vec{i}_{r'r} & |\vec{r}-\vec{r}_c'| \gg \Delta_x, \Delta_y \\ \sum_b^{subcells} \frac{\Delta_{sx}\Delta_{sy}}{\Delta_x\Delta_y}\frac{\hat{\rho}_{c,1}(x_b-\Delta_x)(y_b-\Delta_y)-\hat{\rho}_{c,2}x_b(y_b-\Delta_y)-\hat{\rho}_{c,3}(x_b-\Delta_x)y+\hat{\rho}_{c,4}x_by_b}{|\vec{r}-\vec{r}_c'|^2}\vec{i}_{r'r} & \text{otherwise} \end{cases} \qquad (9)$$

where $\vec{r}_c'$ the center location of cell c and $\vec{r}_b'$ is the center location of sub-cell b. The criterion that $|\vec{r}-\vec{r}_c'|\gg\Delta_x, \Delta_y$ was chosen since this guarantees that no part of the cell surface may be close to $\vec{r}$. Numerically, some real threshold value must be established for $|\vec{r}-\vec{r}_c'|/\Delta_x, \Delta_y$, which by adjustment will trade between accuracy and speed. When the cell must be divided into sub-cells a similar threshold criterion can be used in determining the required number of sub-cells. FIGS. 11 and 12 shows the representation of the cell charge as a single point charge and the subdivision of a cell into sub-cells each containing a point charge.

With the surface charge density defined in terms of unknown parameters (charge density at cell corners) and a method for calculating the perturbation electric field, the boundary condition on charge conservation can now be enforced at the surfaces. The electric field on the conducting side of a surface $\hat{E}_s$ in (2) is now replaced with the total electric field such that:

$$\vec{n} \cdot \sigma_M(\vec{E}_0(\vec{r}) + \vec{E}_1(\vec{r})) = -j\omega\hat{\rho}_{fs} \qquad (10)$$

In the true solution this equation would be exact at every point, however with a finite number of parameters defining the charge distribution there is no guarantee that the available charge distributions will fall exactly into the true solution space. Therefore the best one can hope for is that the error in (10) is generally small, such that the solution is approximately true (note that here true refers the solution to the perturbation problem with its assumptions which is usually not equal to the true full solution to the notch problem). Numeric techniques often handle the problem of not having solutions covering the complete solution space by integrating (10) over a finite number of areas usually equal to the number of unknowns and imposing the resulting set of equations in lieu of the original boundary condition equation. In FE techniques the integration is normally accompanied by weighting functions, which under special conditions can guarantee the solution found is the closest of the available solutions to the actual solution in the norm sense.

The method of collocation chooses the weighting functions as impulses, which does not guarantee the closest solution, but allows for the rapid generation of the set of equations defining the solution. This method is equivalent to enforcing (10) at a number of locations equal to the number of unknown. Therefore the surface locations of enforcement are chosen to coincide with the cell corners that are free parameters (i.e., corners not being interpolated from another cell's edge).

The final difficulty that lies in building the set of equations to be solved pertains to the evaluation of $\vec{E}_1(\vec{r})$ with $\vec{r}$ positioned an incremental distance from the surface at the locations where (10) is being enforced. The issue can be observed in equation (6) when the summations reaches the cells near the point at which $\vec{E}_1(\vec{r})$ is being evaluated. Here the quantity $|\vec{r} - \vec{r}\,'|$ will approach zero and subdividing the cells into more and more sub-cells will only result in values of $|\vec{r} - \vec{r}\,'_b|$ becoming closer to zero. Numerically this will result in a summation of large values that will not have an appropriate convergence to a finite value.

Since the boundary condition only requires the normal component of the field, the contributions from the coplanar cells can be handled in a numerically stable way. The continuity (jump) condition relating the electric field to the surface charge is:

$$\vec{n} \cdot \|\vec{E}\| = \frac{\hat{\rho}_{fs}}{\varepsilon_0} \qquad (11)$$

when only free charge is present as is the immediate case. If only surface charge coplanar to the plane on which the boundary condition of (10) is being enforced is considered, the electric field will be symmetric about the plane and therefore:

$$\vec{n} \cdot \vec{E} = \frac{\hat{\rho}_{fs}}{2\varepsilon_0} \qquad (12)$$

where $\vec{E}$ is the field on the on the surface normal side of the boundary. The normal electric field contribution from all of the charge in the plane is then simply related to the surface charge density at the location of the boundary condition. The set of equations which must be solved for the surface charge parameters are then described by:

$$-\vec{n}_l \cdot \vec{E}_1(\vec{r}_l) - \frac{j\omega}{\sigma_M}\hat{\rho}_{fs}(\vec{r}_l) = \vec{n}_l \cdot \vec{E}_0(\vec{r}_l) \; l = 0, 1, \ldots, L-1 \qquad (13)$$

where L is the number of cell corner locations at which the boundary condition is being imposed, $\vec{r}_l$ is the location of the lth cell corner, $\vec{n}_l$ is the surface normal (pointing into the conducting region) of the cell for which $\vec{r}_l$ is a corner, and where the normal electric field is determined by:

$$\hat{n}_l \cdot \vec{E}_1(\vec{r}_l) = \frac{\hat{\rho}_{fs}(\vec{r}_l)}{2\varepsilon_0} + \frac{1}{4\pi\varepsilon_0} \sum_{p \in P}^{\substack{surface \\ regions}} \sum_c^{cells} \begin{cases} \dfrac{\Delta_x \Delta_y}{4} \dfrac{(\hat{\rho}_{c,1} + \hat{\rho}_{c,2} + \hat{\rho}_{c,3} + \hat{\rho}_{c,4})}{|\vec{r}_l - \vec{r}'_c|^2}(\vec{n}_l \cdot \vec{i}_{l'_r}) & |\vec{r} - \vec{r}'_c| \gg \Delta_x, \Delta_y \\ \sum_b^{subcells} \dfrac{\Delta_{sx}\Delta_{sy}}{\Delta_x \Delta_y} \dfrac{\hat{\rho}_{c,1}(x_b - \Delta_x)(y_b - \Delta_y) - \hat{\rho}_{c,2}x_b(y_b - \Delta_y) - \hat{\rho}_{c,3}(x_b - \Delta_x)y + \hat{\rho}_{c,4}x_b y_b}{|\vec{r}_l - \vec{r}'_c|^2}(\vec{n}_l \cdot \vec{i}_{l'_r}) & \text{otherwise} \end{cases} \qquad (14)$$

where P is the set of regions not coplanar to the cell for which $\vec{r}_l$ is a corner.

Although it may appear that a sufficient number of equations can be created from (13) to match the number of unknowns, these equations are not completely independent and one additional equation is required. In the unperturbed state (i.e., the MUT with no notch) the current in the MUT has no divergence and there is also no accumulated charge. Since perturbation from the notch decays with the distance from the notch, the limit of the closed surface integral of the current will approach zero as the surface is moved away from the notch. This indicates no net charge should be enclosed in the volume that this surface surrounds. Since all the charge in the system has been located on the bilinear interpolation cells, the integral of the charge over all cells must be zero also. Since the net charge in each cell can be determined by (7) this constraint can be expressed as:

$$\sum_{regions}^{surface} \sum_{c}^{cells} \frac{\Delta_x \Delta_y}{4} (\hat{\rho}_{c,1} + \hat{\rho}_{c,2} + \hat{\rho}_{c,3} + \hat{\rho}_{c,4}) = 0 \quad (15)$$

The equation formed by (13) and (15) are all linear in terms of the unknowns and therefore they can be arranged into the matrix form:

$$M\rho = E_0 \quad (16)$$

where M contains the coefficients of the charge density parameters, $\rho$ is the vector of charge density parameters, and $E_0$ is the vector of unperturbed field values from the right hand side (RHS) of (13) and the single zero from the RHS of (15).

It is useful to note that in forming the matrix M, no specific information was included about the unperturbed electric field $\overline{E}_0(\vec{r})$ (although the matrix does contain information about the frequency $\omega$). This is significant with respect to computational efficiency because the matrix M can be factored once into an LU form (lower triangular times an upper triangular matrix), which can then be used to rapidly solve for $\rho$ with different RHS vectors $E_0$ by back substitution (strictly, M is a rectangular matrix due to the additional equation on total charge, since it is known that this is an independent equation it can be added to any of the other equations to preserve M as square). In practice, this allows for the sensor position to be translated with respect to the MUT or rotated parallel to the MUT surface with no computational effort spent on recalculating matrix coefficients or factoring the matrix. In these cases the majority of the computation will result from the remaining task of computing volume perturbation currents and their affect on terminal voltages.

The approximate perturbation in the sensing element voltage can now be calculated by the application of Faraday's Integral Law to the mean contour of the winding by assuming that the winding forming the element has zero perturbation current density and therefore a zero electric field inside. The resulting expression for the perturbation voltage is:

$$\hat{v}_p = j\omega \oint_C \overline{A}_p(\vec{r}) \cdot d\vec{s} \quad (17)$$

where $\overline{A}_p(\vec{r})$ is the perturbation in the magnetic vector potential. The perturbation in the vector potential is due to the perturbation currents throughout the volume and can be determined from the superposition integral for the vector potential:

$$\overline{A}_p(\vec{r}) = \frac{\mu_0}{4\pi} \int_V \frac{\overline{J}_p(\vec{r}')}{|\vec{r} - \vec{r}'|} dV \quad (18)$$

The perturbation current $\overline{J}_p$ has two components: an additive component resulting from the perturbation currents created by the accumulated surface charge on the outside of the notch denoted by $\overline{J}_{1O}$, and a subtractive component $\overline{J}_{O1}$ resulting from the removal of the unperturbed currents flowing inside the notch. The total perturbation currents are related to the external perturbation field and internal unperturbed electric field by:

$$\overline{J}_p = \overline{J}_{1O} - \overline{J}_{O1} = \sigma_M \overline{E}_{1O} - \sigma_M \overline{E}_{O1} \quad (19)$$

The unperturbed electric fields are determined from the chosen description method of $\overline{E}_0(\vec{r})$ in the problem specification, while the perturbation field is evaluated at any position not coincident with charged surfaces by using the solution vector $\rho$ and (9).

In order to avoid a complex expression involving the integration of the terms of the sum found in (9) along with the issues associated with incremental distances from charged surfaces and the likely numerical representation of $\overline{E}_0(\vec{r})$, the integral of (18) will be evaluated numerically. The volume of integration will be divided up into volumetric cells. The integral has the behavior that as the distance $|\vec{r} - \vec{r}'|$ becomes large compared to the cell size, the actual distribution of $\overline{J}_p$ within the cell becomes unimportant. The minimal distance from the current in the MUT to the locations where it will be necessary to evaluate the vector potential for the contour integrals is also limited since the sensing element is offset from the surface of the MUT. Therefore (18) can be reduced to:

$$\overline{A}_p(\vec{r}) = \frac{\mu_0}{4\pi} \sum_d^{Volume\ Cells} \frac{\overline{\alpha}_d}{|\vec{r} - \vec{r}_d|} \quad (20)$$

A second approximation is now made in evaluating $\overline{\alpha}_d$, which is the integral of the perturbation current over the volumetric cell with index d. Since the current density determined by $\overline{E}_1(\vec{r})$ and $\overline{E}_0(\vec{r})$ are both expected to be continuous in their corresponding integration volumes, it is possible to choose a small enough cell size such that $\overline{\alpha}_d$ is well approximated by:

$$\overline{\alpha}_d = V_d \begin{cases} -\sigma_M \overline{E}_0(\vec{r}_d) & d \in \text{internal cell indices} \\ \sigma_M \overline{E}_1(\vec{r}_d) & d \in \text{external cell indices} \end{cases} \quad (21)$$

where $V_d$ is the volume of the dth cell. The division of the volume into volumetric cells is a matter of optimizing cell size as compared to both distance to the point at which $\overline{A}_p$ is being evaluated and the spatial dependence of the current density in the vicinity of the cell.

Figure 13:
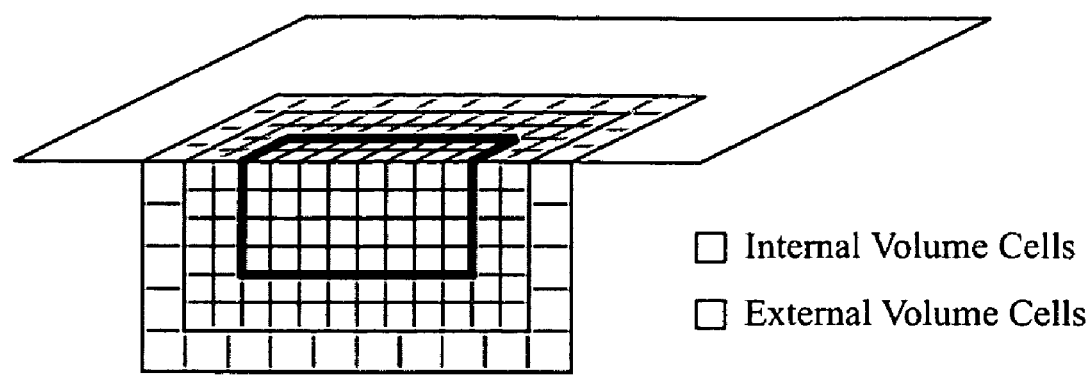
FIG. 13 shows a cross-sectional view of volume cell layout for perturbation currents used in calculating the perturbation of the vector potential.

The structure of the volume cell layout used is shown in FIG. 13. It is composed of skins of cells of a similar size surrounding the available faces of the notch. Each successive skin is chosen to have an increasing thickness and cell size since it is expected that the fields from the charge sources will become more diffuse with position. It is assumed that the larger cells will be kept small enough such that the distance to the sensing element will be large in comparison and the preceding approximations will be valid or alternatively these cells will make minimal contribution as a result of containing a minimal current density. The extent of the skins around the notch is chosen such that perturbation currents in the remaining MUT volume do not produce significant errors. The volume inside the notch is then divided into equally sized cells. The contour of the sensing element which must be followed in the integral of (17) is generally composed of linear segments as is the case of a rectangular winding. Therefore by substituting the result for the perturbation vector potential found in (20), and changing the integral of (17) to a sum of contour integrals over linear segments, the following expression is produced:

$$\hat{v}_p = \frac{j\omega\mu_0}{4\pi} \sum_{g=0}^{G-1} \sum_{d}^{Volume\ Cells} \int_{\vec{r}_g}^{\vec{r}_{g+1}} \frac{\overline{\alpha}_d}{|\vec{r}(s) - \vec{r}_d|} \cdot d\vec{s} \quad (22)$$

where $\vec{r}_g$ is the location of the gth node of the linear segments defining the total contour from the positive to the negative terminal of the sensing element, G is the total number of nodes defining the contour, and s is the distance along the contour path. Since the path of the contour is a straight line and the quantity $\overline{\alpha}_d$ is not dependent on the position along the path, the dot product can be moved outside the integral by replacing $d\vec{s}$ with $\vec{i}_g ds$, where:

$$\vec{i}_g = \frac{\vec{r}_{g+1} - \vec{r}_g}{|\vec{r}_{g+1} - \vec{r}_g|} \quad (23)$$

The remaining position vector $\vec{r}$ can then be represented parametrically in s for the segment starting with the gth node as:

$$\vec{r}(s) = \left(x_g + \delta_x \frac{s}{\delta}\right)\vec{x} + \left(y_g + \delta_y \frac{s}{\delta}\right)\vec{y} + \left(z_g + \delta_z \frac{s}{\delta}\right)\vec{z} \quad (24)$$

where $\delta = |\vec{r}_{g+1} - \vec{r}_g|$, the quantities $\delta_x, \delta_y, \delta_z$ correspond to the proper vector component of $(\vec{r}_{g+1} - \vec{r}_g)$, the quantities $x_g, y_g, z_g$ correspond to the components of $\vec{r}_g$, and s=0 has been set to correspond to the position along the path at $\vec{r}_g$. The expression for (22) can now be expressed as:

$$\hat{v}_p = \frac{j\omega\mu_0}{4\pi} \sum_{g=0}^{G-1} \sum_{d}^{Volume\ Cells} (\overline{\alpha}_d \cdot \vec{i}_g) \quad (25)$$

$$\int_0^{\delta} \left( \left(x_g + \delta_x \frac{s}{\delta} - x_d\right)^2 + \left(y_g + \delta_y \frac{s}{\delta} - y_d\right)^2 + \left(z_g + \delta_z \frac{s}{\delta} - z_d\right)^2 \right)^{-1/2} ds$$

where $x_d, y_d, z_d$ are the vector components of $\vec{r}_d$. The integrand of (25) can be simplified, resulting in:

$$\hat{v}_p = \frac{j\omega\mu_0}{4\pi} \sum_{g=0}^{G-1} \sum_{d}^{Volume\ Cells} (\overline{J}_d \cdot \vec{i}_g) \quad (26)$$

-continued $$\int_0^{\delta} \left(s^2 + s\frac{2}{\delta}(\vec{r}_{g+1} - \vec{r}_g) \cdot (\vec{r}_g - \vec{r}_d) + |\vec{r}_g - \vec{r}_d|^2\right)^{-1/2} ds$$

For which the integral can be solved analytically giving the expression for the perturbation in the terminal voltage of a sensing element:

$$\hat{v}_p = \frac{j\omega\mu_0}{4\pi} \sum_{g=0}^{G-1} \sum_{d}^{Volume\ Cells} (\overline{\alpha}_d \cdot \vec{i}_g) \ln \frac{2\sqrt{\delta^2 + C + \delta_{dg}^2} + 2\delta + \frac{C}{\delta}}{2\delta_{dg} + \frac{C}{\delta}} \quad (27)$$

where $C = 2(\vec{r}_{g+1} - \vec{r}_g) \cdot (\vec{r}_g - \vec{r}_d)$ and $\delta_{dg} = |\vec{r}_g - \vec{r}_d|$.

Thus far it has been assumed that the unperturbed electric field $\vec{E}_0(\vec{r})$, used in forming the vector $E_0$ for the system matrix equation, can be simply calculated at will; depending on the modeling techniques utilized, their evaluation may be computational expensive. When simulations are being performed where, for example, a notch is being translated across the MUT surface or rotated in the plane of the MUT this would often result in repetitive computation of unperturbed fields at similar locations. Therefore, in practice, it is often useful to evaluate the unperturbed fields in the region of interest on regular grid intervals before starting notch perturbation simulations. Assuming that a sufficient density of points can be included in the region, the unperturbed electric field can be calculated at the specific points required from the regular grid using linear or other higher order interpolation schemes with sufficiently small error. In addition to the reduction in redundant computation, this method of evaluating the electric field simplifies the required dynamic interaction between implementations of the perturbed and unperturbed models.

It is worth commenting on some of the possible issues surrounding the application of a perturbation model for a notch as described. The chosen perturbing effects of the notch have been introduced to resolve two basic conflicts with the unperturbed model, created by its presence. These conflicts consist of the nonzero current density of the unperturbed model in the nonconducting region of the notch and the divergent current density at the notch surfaces which results from subtracting these currents. The divergence of the current at the other MUT surfaces, which arises as a result of addressing the two preceeding conflicts, is also accounted for. However, in a system in which the MUT is magnetically permeable, the presence of the notch also creates a conflict in the relation between the magnetic field intensity $\overline{H}$ and the magnetic flux density $\overline{B}$. This can also be looked upon as a conflict in the continuity of magnetic flux density across the notch surfaces. This may be addressed by the inclusion of perturbation magnetization currents in the model.

As a simple illustration of the use of this method, a uniform magnetic field, tangential to the surface, is assumed. This results in a current density of the form $\vec{J} = e^{z(1+j)/\delta}\vec{y}$, where $\delta$ is the standard skin depth. This excitation was chosen because of the symmetry about the notch for the solution, the simplicity in calculating the unperturbed electric fields in the MUT, and direct relation between the standard skin depth equation and that of the unperturbed solution. The notch for these simulations was chosen to be surface breaking in an infinitely thick MUT with the dimensions of 250×50×125 μm. The length to depth ratio of 2:1 was chosen because it is the typical aspect ratio of a surface breaking crack under uniaxial loading conditions. The 50 μm notch width was chosen such that charge distributions on edge surfaces would be observable in figures, in addition to being comparable with the dimensions of notches produced by electric discharge machining (EDM) techniques.

Simulations were conducted for current distributions with three different skin depths equal to one third, one, and three times the notch depth. This range of skin depth is sufficient to allow the determination of current distribution regimes where the perturbation model may become inaccurate by the observation of unexpected field behavior. To better observe the behavior of the current distributions, two types of plots have been included for each unperturbed skin depth.

The first type of plot only includes information about the magnitude of the time-harmonic representation of the surface charge density and current density. Since the surface charge is a scalar quantity located on the notch and MUT surfaces only, it is directly indicated. To avoid obstructing the sides of the notch, the surface charge density on the MUT surface has been partially cut away. In comparison to the surface charge density, the current density is a vector quantity located throughout the volume and therefore is only indicated on two planes. One plane is positioned away from the notch such that the current density is equivalent to the unperturbed quantity, while the other cuts through the center of the notch; both planes are oriented normal to the unperturbed current direction. The component of the current density normal to these planes is indicated in each plot, however, due to the symmetry of the problem and the chosen plane locations, the current density is normal to these planes and therefore no vector information is lost.

The second type of plot includes information on the instantaneous values of current and charge density for a chosen phase of the sinusoidal cycle. The electric field lines or equivalently the lines of current flow are generally changing with time, due to the phase dependence of the unperturbed current density as a function of depth and therefore must be visualized at a specific instance of time within the periodic cycle. Each plot contains six field lines labeled a through with starting coordinates: a—(125, 300, −δ/2), b—(75, 300, −δ/2 ), c—(25, 300, −δ/2), d—(−25, 300, −δ/5), e—(−75, 300, −δ/5), and f—(−125, 300, −δ/5). The instantaneous charge density is also shown on the notch surfaces in addition to the MUT surface. However, the charge density on the MUT surface has been plotted, such that its transparency is inversely related to its intensity, to keep it from visually obscuring the field lines. In addition, the current density normal to a plane is displayed in a region away from the notch where the current density is approximately that of the unperturbed density.

An important characteristic of the unperturbed field with respect to the instantaneous phase is the location of planes parallel to the surface where the current density is exactly zero. The location of these planes can be calculated from the expression for the current density as:

$$z = \delta\left(n\frac{\pi}{2} - \omega t\right) \text{ for integer } n \quad (28)$$

The zero current planes, which are located near the MUT surface and intersect the notch, will be relevant in understanding field line behavior in later discussion.

Figure 14:
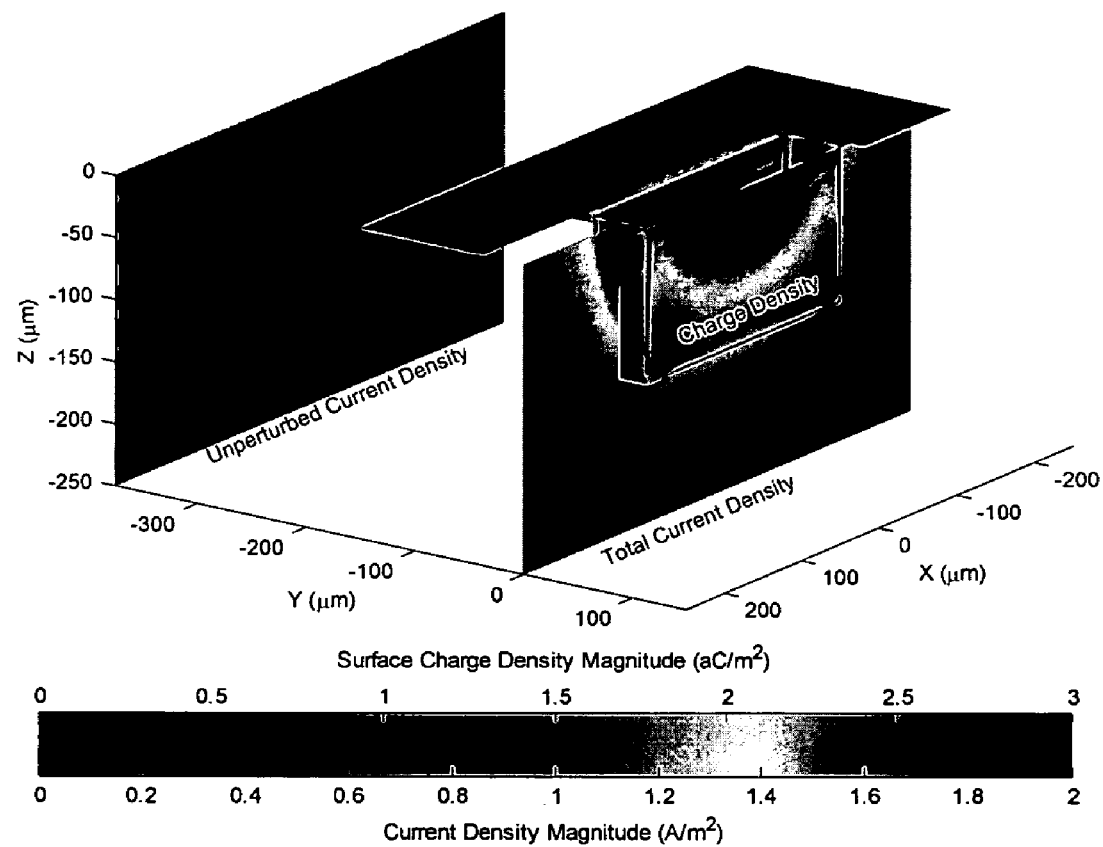
FIG. 14 shows a nominal plot of the current and charge densities in the vicinity of a rectangular notch with the skin depth three times the depth of the notch.

Consider the case where the skin depth is three times as large as the notch depth. Since the skin depth is significantly larger than the notch depth, this case starts to approach the case of a notch in an infinitely long homogeneous conductor where the skin effect is neglected. FIG. 14 shows the resulting intensification of the current density around both the bottom and sides of the notch. The charge density on the notch surfaces normal to the direction of the unperturbed current density forms in order to cancel the unperturbed currents at these surfaces. However, the charge on the notch surfaces results in electric field components normal to the MUT surface. Surface charge on these MUT surfaces must form in order to keep the boundary conditions satisfied. The charge on the MUT surfaces tends to counter the electric field on notch surfaces and thus requires the surface charge on the notch surfaces near the MUT surfaces to intensify to continue to meet boundary conditions. This back and forth effect is responsible for the high charge concentrations at both notch and MUT edges in the final solution.

Figure 15:
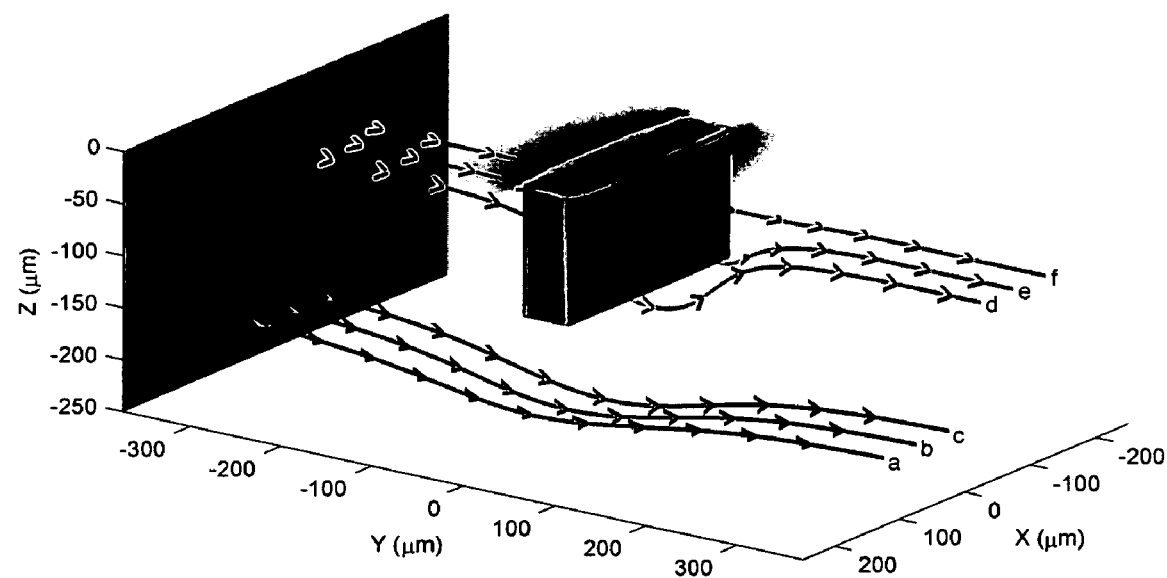
FIG. 15 shows field lines, current density and surface charge density for a relative phase of $\omega t = 0$ for a skin depth three times larger than the notch depth.

The representative instantaneous plot of FIG. 15 illustrates the current flow pattern near the notch. Field lines a through c are significantly below the notch and are therefore mildly impacted, while field lines d and e which would pass directly through the notch in the unperturbed current density are forced under and around. A comparison of the field lines between the two plotted phases shows a minimal difference in current paths. The large skin depth as compared to the notch depth results in a minimal shift in phase of the unperturbed currents in the region of the notch. Coupled with the reduced variation in the unperturbed current density with depth, this produces instantaneous distributions which are generally similar to those of a DC conduction case. The exception to this is during the phase of the cycle when the zero current plane intersects the notch. The location of the zero current plane is significantly below the notch in both instantaneous field plots, where it is located for most of the cycle. During the short period of the cycle when the zero current plane intersects the notch, the field lines are significantly different from those plotted due to the existence of unperturbed current flow in opposing directions on opposite sides of the zero current plane.

Figure 16:
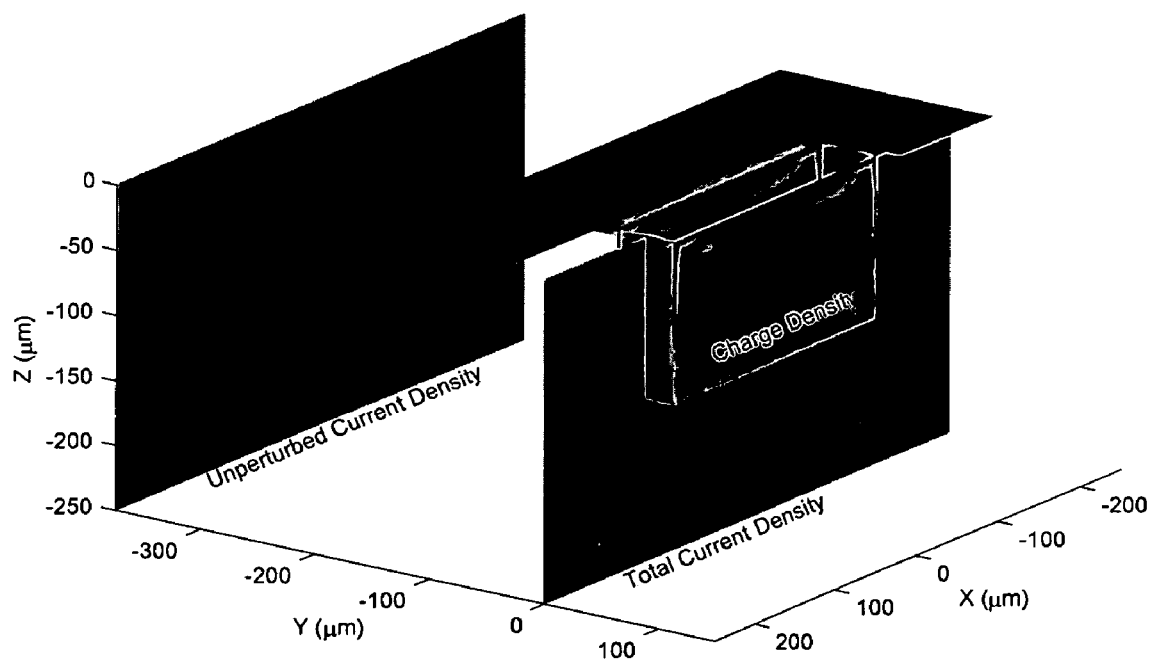
FIG. 16 shows a nominal plot of the current and charge densities in the vicinity of a rectangular notch with the skin depth equal to the depth of the notch.
Figure 17:
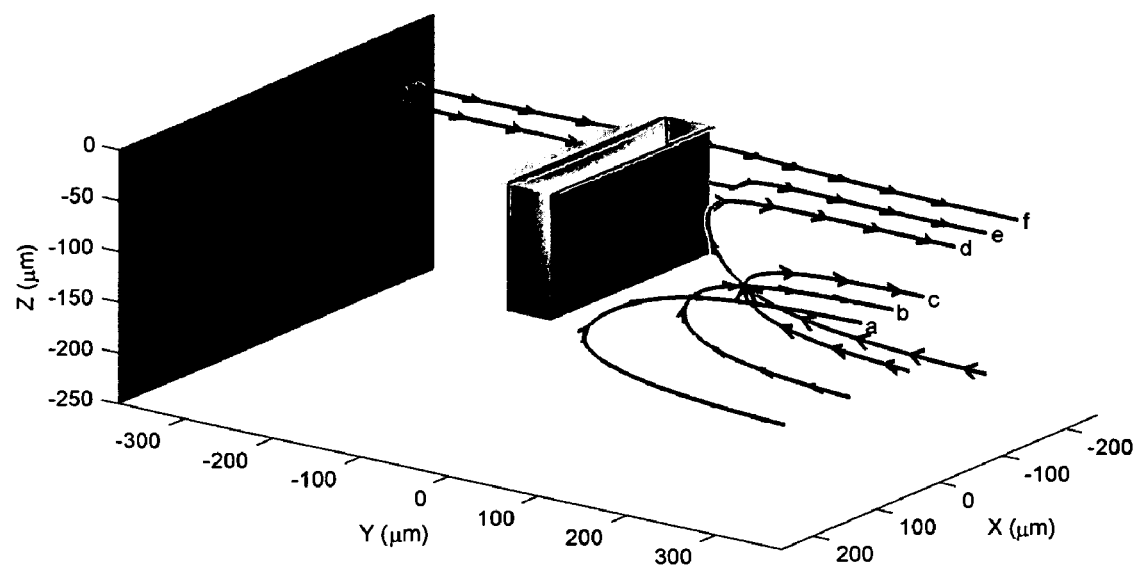
FIG. 17 shows field lines, current density and surface charge density for a relative phase of $\omega t = -\pi/4$ for a skin depth equal to the notch depth.

The reduction of the skin depth so that it is equal to that of the notch depth produces the plot of quantity magnitudes shown in FIG. 16. Here it can be seen that a greater portion of the current is traveling around the sides of the notch due to the greater current density near the surface. The instantaneous plot shown in FIG. 17 again shows the current flow near the notch. The field line c takes the largest excursion away from the notch, but seems feasible when compared to the skin depth for the MUT. It also shows that the field lines can change dramatically when the zero current plane intersects the notch. The field lines e and f near the surface take the normal path around the notch, however field lines a through d can be seen to reverse direction about the zero plane. Since there is unperturbed current flow both toward and away from the notch surface it seems reasonable for some portion of the current to return following this path, but this effect is now beyond comparison of a pure conduction problem. These effects become even more pronounces when the skin depth becomes small compared to the notch depth. All of the preceding simulations oriented the notch such that its faces were either parallel or normal to the direction of the exponential current density distribution in the MUT. The resulting symmetry in the current and charge distributions verify the implementation of the perturbation model. The goal of the next simulation is to demonstrate the application of the model with an orientation of 45 degrees in the x-y plane such that the resulting symmetry in the fields is broken. The depth dependence of the unperturbed current density is identical to that used previously; however, the rotation results in the following expression for dependence of its vector components on rotation:

$$\vec{J} = e^{\bar{z}(1+j)/\delta}(\vec{x}\sin\theta + \vec{y}\cos\theta) \quad (29)$$

It is again emphasized that this rotation of the unperturbed current does not require the reformulation or re-factoring of the matrix used to evaluate the surface charge density and therefore the surface charge density can be rapidly calculated for any rotation. The simulation results for a skin depth of 375 µm and a rotation angle of 45 degrees are similar to those shown in FIGS. 15 and 17.

The perturbation modeling technique was also tested by comparison with measurement data provided by an MWM array. Measurements were performed on metals containing surface breaking notches created through EDM methods and actual surface breaking cracks produced by cyclic fatigue. The EDM notches provide measurement data for which the actual notch shape and dimensions are known to a sufficient accuracy. In contrast to the notches, the subsurface structure of an actual crack is of much less certain and is often inferred from surface characteristics such as length. The measurement of these cracks demonstrates the practical use of the modeling approach for use in the estimation of crack size when a rectangular shape is assumed in place of the complex and unknown morphology of an actual crack. The prediction of the impedance response, as the sensor is scanned over a notch, results from the combination of the layered-media modeling techniques described in pending U.S. patent application Ser. No. 10/963,482 filed on Oct. 12, 2004, which published as U.S. Patent Application Publication 2005/0127908, and the perturbation model. In the absence of either feature, the MUT can typically be approximated as having electrical properties which are constant over an area of the MUT surface having dimensions similar to the features of interest. Since the impedance data generated by scanning the sensor over the feature will be primarily influenced by its presence at the point when the sensor's windings are in close proximity to the feature, impedance data on the perimeter of that affected can be used to estimate electrical properties. These electrical properties can then be used in the layered models to evaluate the current distribution within the material in the absence of a notch, which serves as the unperturbed current distribution required by the perturbation model. By translating this current distribution relative to the modeled notch and simultaneously translating the paths of(27), which correspond to the locations of the secondary sensing elements, the perturbation of the secondary voltage as a function of position is calculated. The resulting impedance response in the vicinity of the notch is calculated by:

$$\hat{Z}_{1,n} = \hat{Z}_0 + \frac{\hat{v}_{p,n}}{\hat{i}_0} \quad (30)$$

where $\hat{Z}_0$ is the impedance of the sensor in the absence of the notch based on an assumed layered material structure, $\hat{i}_0$ is the excitation current used to determine the unperturbed current distribution, and $\hat{v}_{p,n}$ is the perturbation voltage on the nth secondary winding.

Figure 18:
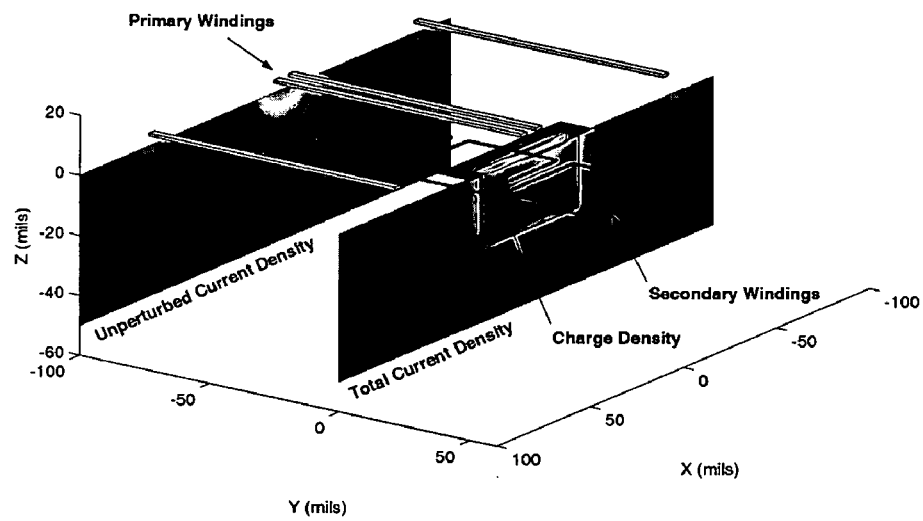
FIG. 18 shows the current and charge densities in the vicinity of a notch for a sensor array positioned over the notch.

The array used for measurements was similar in construction to that shown in FIG. 4. The row of sensing elements was centered in the space between the primary winding pair and the single outer primary winding. In addition, the narrow dimension of the box describing the perimeter of the primary windings was 3.7 mm (0.145 in.). The relative positioning of the primary windings and sensing elements is represented in FIG. 18. The unperturbed current density is shown on a plane at y=−0.1 in. while the notch's effect on the current density is shown for a plane at y=0 in. The surface of the notch and the partially shown MUT surface display the surface charge density. With the x position of the sensor defined relative to the center of the gap between the pair of primary windings, distributions are shown for the sensor positioned at x=−0.01 in. Measurements were made with the sensor mounted to a motorized scanning apparatus which traversed the material containing the notch or crack. This allowed the measured impedance data to be recorded along with position information for more direct comparison with theoretical responses. Before making measurements, the measurement system was calibrated using the response of the array in air and the response with a shunted sensor.

Since the greatest response is expected when the feature interrupts the greatest amount of current, the long dimension of the notch or crack was oriented perpendicular to the main direction of induced eddy currents within the material. Although the perturbation analysis technique allows for the arbitrary positioning of the notch relative to the sensor, the feature was positioned such that it would fall directly below a single sensing element in order to simplify comparisons. This was accomplished by locating the sensing elements within the measured data which indicated a response to the feature, adjusting the position of the sensor in a direction orthogonal to the scan direction, and repeating the scan until the response was primarily contained within the measurements of a single sensing element.

Measurements were made on three EDM notches of differing sizes located within a stainless steel material with a thickness of 0.050 in. (1.27 mm). Each of the notches had an approximate width of 0.005 in.(0.127 mm) and a depth equal to one half the length, such that the cross-section was semicircular in shape. The three notches measured were 0.030, 0.050, and 0.090 in. (0.762, 1.27, and 2.29 mm) in length. Although the notches were semicircular in geometry, the existing numerical implementation of the perturbation model required a rectangular notch geometry which was the geometry used in all simulated responses. FIG. 18 shows current and charge density distributions associated with the 0.050×0.025×0.005 in. notch at an excitation frequency of 316 kHz.

Figure 19:
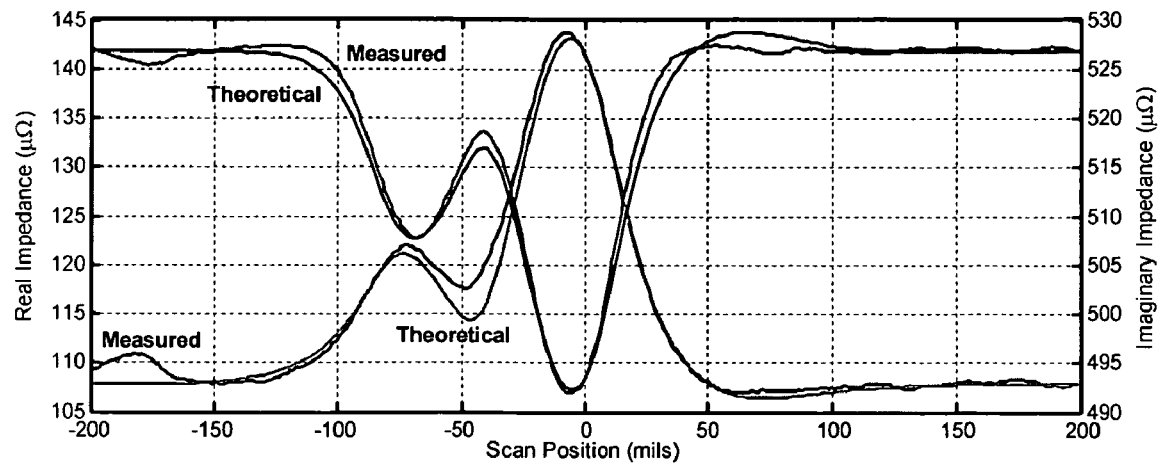
FIG. 19 shows a comparison of the measured and predicted impedance response as a sensor is scanned over a 0.060×0.024 in. crack at an excitation frequency of 316 kHz.
Figure 20:
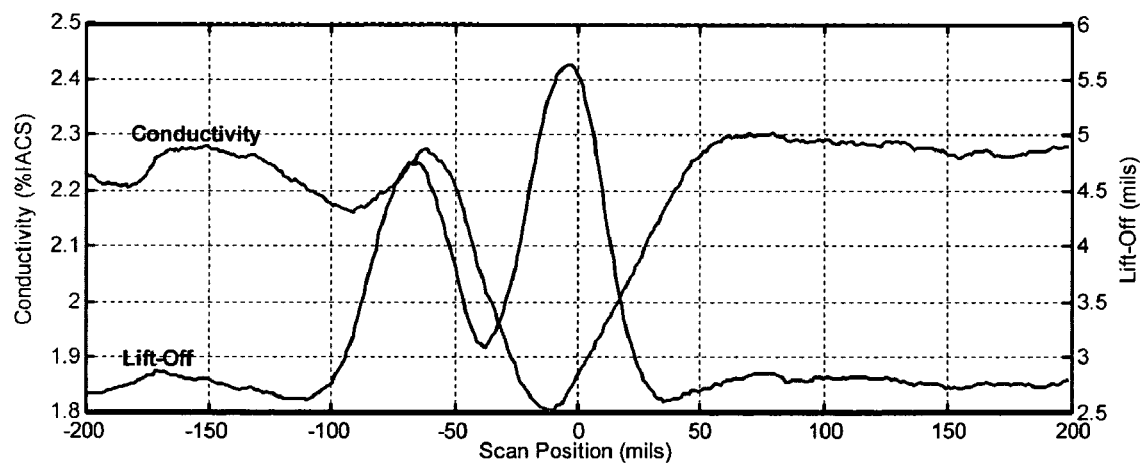
FIG. 20 shows estimated material properties based on the data of FIG. 19 and the assumption of a MUT with uniform electrical properties.

Since the thickness of the material is known, the conductivity of the material and lift-off of the sensor can be determined from a single frequency measurement of the impedance in areas away from the notch. These values are readily determined from two-dimensional measurement grids. FIGS. 19 and 20 present material property data based on such a layered media model and the impedance data obtained. The peaking in the conductivity and lift-off data for scan positions in the range of −0.100 to 0.050 in. is a result of the uniform layered material property model not representing the presence of a notch. However, away from the notch, a reasonable estimate of the material properties can be obtained from the data; the estimated values have been used in the calculation of the unperturbed current density indicated in FIG. 18. With a conductivity value of 2.28% IACS, the skin depth at 316 kHz is 0.0306 in., which allows significant penetration of the induced currents over the depth of the notch.

FIG. 18 also shows information about the current density for a plane located at y=0, which cuts down the center of the notch. Since the interior of the notch is assumed to be composed of nonconducting material, the current density is exactly zero for the associated rectangular section of this plane. The increased current density resulting from the disruption of currents around the notch can be seen along the notch perimeter. The surface charge density is indicated for a portion of the MUT surface surrounding the location at which the notch breaks the surface and on the near surfaces of the notch. The surface charge on the large rectangular face of the notch can be seen as distributed in such a way as to counter the unperturbed current density.

In order to compare the predicted impedance response and the measured impedance response, the measured data was first shifted along the scan direction to provide good agreement between the shapes of the responses. This was necessary due to the difficulty in accurately adjusting the position of the sensor relative to position of the notch to a known distance during data acquisition. Initial comparisons between the measured impedance response and those produced by (30) revealed that although the structure of the theoretical response was in good agreement, the magnitude of the response varied from that predicted by more than a factor of 2. Several possible sources of this discrepancy exist including: the semicircular nature of the notch as compared to the rectangular model, non-canceling numerical errors resulting from the use of one model for the predicting the unperturbed current density and a different for evaluating the perturbation response, approximation errors resulting from ignoring diffusion effects in the perturbation currents, mathematical errors, and implementation errors. Due to the difficulty in resolving the source of this type of error and the good response shape agreement, a frequency dependent complex correction factor was chosen to scale the perturbation in the impedance response such that the impedance response is determined by:

$$\hat{Z}_{1,n} = \hat{Z}_0 + \hat{C}\frac{\hat{v}_{p,n}}{\hat{i}_0} \quad (31)$$

where $\hat{C}$ is an empirically determined correction factor. In order to determine the value for this correction factor, the best fit scale factor was evaluated for each notch size. In this case the best fit was chosen to minimize the error between the measured and theoretical response over a defined range of the response data. The error in the range $x_1 \leq x \leq x_2$ is characterized by:

$$Error^2 = \int_{x_1}^{x_2} \left|(\hat{Z}_m(x) - \hat{Z}_0 - \hat{C}\hat{Z}_t(x))\right|^2 dx \quad (32)$$

where $\hat{Z}_m(x)$ is the measured impedance response, and:

$$\hat{Z}_t = \frac{\hat{v}_{p,n}}{\hat{i}_0} \quad (33)$$

The quantity $\hat{Z}_0$ is subtracted from the measured response due to the fact that the correction factor effects only the deviation in the predicted response from this value. Since both measured and theoretical responses are known only numerically, the best fit correction factor which minimizes the error can be determined from:

$$\hat{C} = \frac{Z_t^H(Z_m - \hat{Z}_0)}{\|Z_t\|^2} \quad (34)$$

where $Z_t$ and $Z_m$ are column vectors containing values sampled from $\hat{Z}_m(x)$ and $\hat{Z}_t(x)$ at regular intervals on the interval $x_1 \leq x \leq x_2$.

TABLE 1

Complex scale factors and resulting error density determined from the measured and predicted sensor response for notches with known dimensions.

| | 316 kHz | | | 3.16 MHz | | |
|---|---|---|---|---|---|---|
| Notch Size (mils) | Best Fit Scale Factor (mag ∠ phase°) | Best Fit Error (%) | Average Error (%) | Best Fit Scale Factor (mag ∠ phase°) | Best Fit Error (%) | Average Error (%) |
| 30 × 5 × 15 | 0.390 ∠ −17.47 | 0.99 | 1.20 | 0.251 ∠ −24.28 | 5.21 | 5.59 |
| 50 × 5 × 25 | 0.410 ∠ −18.02 | 0.69 | 0.90 | 0.278 ∠ −21.66 | 3.68 | 3.60 |
| 90 × 5 × 45 | 0.424 ∠ −11.19 | 0.68 | 1.48 | 0.319 ∠ −18.81 | 1.85 | 4.22 |
| Average | 0.408 ∠ −15.48 | | | 0.282 ∠ −21.36 | | |

Based on the responses observed for each of the three notches, the correction factor was determined using a scan range of −0.150 in. to +0.150 in. The best fit correction factors calculated for each notch size and measurement frequency are listed in Table 1. The errors presented reflect an "energy" error as a fraction of the "energy" in the corrected response, which is described by:

$$\text{Energy Error} = \frac{\|Z_m - \hat{Z}_0 - \hat{C}Z_t\|^2}{\|\hat{C}Z_t\|^2} \quad (35)$$

The averages of the complex factors from each notch are also indicated in the table along with the errors associated with using the average factor rather than that producing the best fit response. The "Best Fit Error Density" is associated with the "Best Fit Scale Factor" which provides the best fit for a specific notch, while the "Average Error Density" for each notch is based on the use of the average scale factor for the particular measurement frequency. The corrected theoretical response and the measured response of the 0.050× 0.005×0.025 in. notch at 316 kHz are shown in FIG. 19. Similar results were obtained for 0.030×0.005×0.015 in. and 0.090×0.005×0.015 in. notches.

Comparisons of measured and corrected theoretical response were also made for an excitation frequency of 3.16 MHz. As indicated by the tabulated errors, the match between experiment and simulations are not as good as those at 316 kHz. However, they do contain a majority of the significant features of the response structure. For example, the change in shape of the response from a clear double peak to a mostly single peaked response as the length of the notch increases from 0.030 in. to 0.090 in. is captured. In addition, the overall amplitudes of the responses generally track the change in notch size.

Measurements were also performed on samples having real cracks. In this case, there were three cracks of different sizes located in thick titanium plates. Although the true dimensions of these cracks were not exactly known, values exist based on the observable surface length and the use of this length to determine depth values from empirical correlation charts obtained through destructive testing of other samples. The goal here was to compare the impedance response of the measured cracks with the response from the perturbation model using a rectangular representation of the notch. The expected dimensions are initially considered in simulations and errors between measured and theoretical responses are evaluated in order to find alternate crack dimensions which produce a better match in response.

The crack specimens obtained were produced in a laboratory environment by applying a cyclic load to the titanium plates. However, in order to cause crack initiation to occur in a desirable location and to decrease the possibility of multiple initiation sites, EDM notches were created in the plates before loads were applied. The notches have the effect of locally concentrating stresses in their vicinity and therefore promoting the formation of a crack during cyclic fatigue. Since the presence of the notch will in itself produce a significant sensor response, metal is removed from the surface after the fatigue process is complete so that only the crack remains. A variety of crack sizes were produced by the intrinsic variability of the material and by altering parameters of the cyclic loading such as the number of cycles. Since only the surface of the material can be directly observed without a destructive analysis of the material containing the crack, crack size and morphology can only be estimated for intact cracks. This estimation is typically made by performing a destructive analysis on a representative portion of a population of cracks. The resulting data can be used to provide a statistical relation between the directly measurable surface length of a crack and the depth of the crack. However, due to the complex geometry of a typical crack and the degree of randomness in crack growth, it may be difficult to always predict what lies below the surface with accuracy using this method.

Although the actual width of the crack was not directly measured, it may be significantly smaller than either the length or the depth since no material is removed as in the case of an EDM notch. The width is primarily dependent on residual stresses within the material which may either cause the crack to be closed in a local area of compression or pulled open in a local area of tension. Due to the fact that extreme relative dimensions in geometry may lead to errors and excessive computations in reaching a numerical solution, a notch width of 0.002 in. was used for all notch simulations. It is expected that the impedance response will be somewhat independent of width as long as both actual crack and simulated notch width values are small compared to both sensor dimensions and the skin depth. The simulated responses of this section also utilize the correction factors obtained from the EDM notches of the preceding section.

In comparing the measured impedance response of each crack to notches with various dimensions, the degree of match is expressed in terms of an energy error. However, unlike the comparisons of the previous section which used (35), the energy error was expressed relative to the energy of the measured response by:

$$\text{Energy Error} = \frac{\|Z_m - \hat{Z}_0 - \hat{C}Z_t\|^2}{\|Z_m - \hat{Z}_0\|^2} \quad (36)$$

The error was again evaluated over the scan range of −0.150 in. to 0.150 in. for each comparison.

Table 2 presents comparisons for a crack with expected dimensions of 0.034×0.012 in. The comparisons are presented in terms of an energy error relative to the energy of the measured response. The minimal error appears in bold for each measurement frequency and shows reasonable agreement between the predicted and measured responses.

TABLE 2

Comparison between the measured response of a 34 × 12 mil crack and the simulated responses for a variety of notch dimension values.

| Depth (mils) | 316 kHz Error (%) | 3.16 MHz Error (%) |
|---|---|---|
| 6 | 11.37 | 14.05 |
| 8 | 4.62 | 5.67 |
| 10 | 15.32 | 10.34 |

Figure 21:
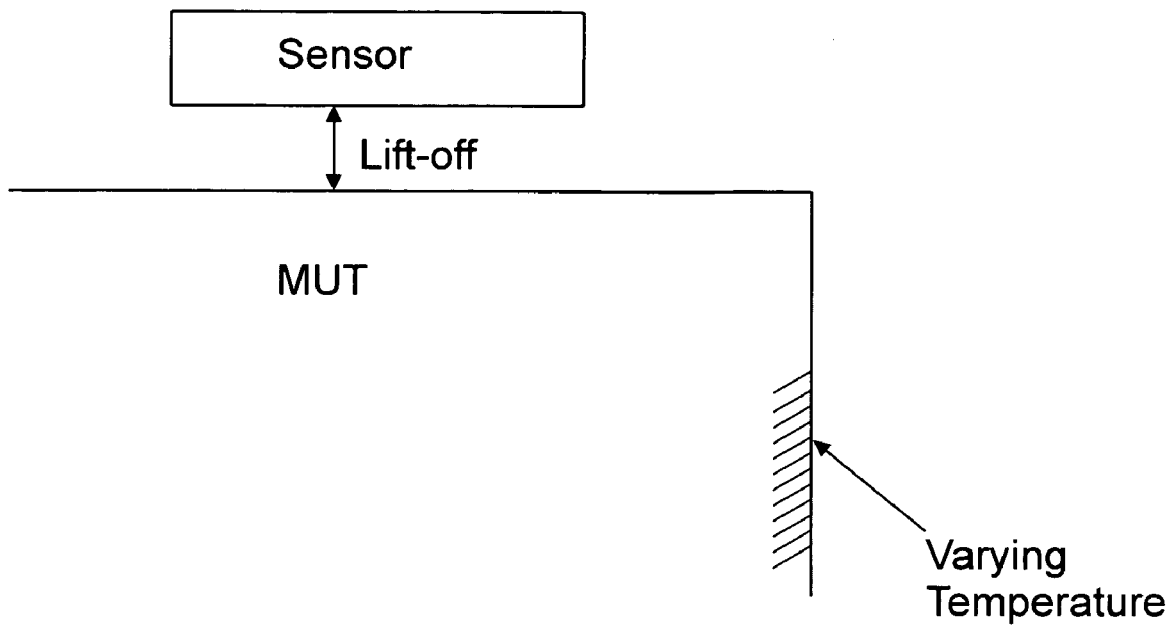
FIG. 21 shows a sensor near the edge of a material for monitoring a hidden temperature variation.

This approach of combining the results of a relatively slow model for determining a nominal field distribution along with a local model for rapidly computing response variations can also be applied to material with complex geometries. An example application is health monitoring of thermal protection systems. Typically the sensor cannot be placed directly in the area of interest and measurements must be performed through or around adjacent materials that may not be exposed to the extreme conditions of the protection system. For example, FIG. 21 shows an MWM sensor near the edge of a test material. This edge introduces significant complexity when trying to model the sensor response. In this case, the temperature variations in on the hidden face are being monitored and the rapid model only needs to be accurate enough to provide a correlation between the sensor response and the properties (e.g., temperature) of the hidden surface.

Figure 22:
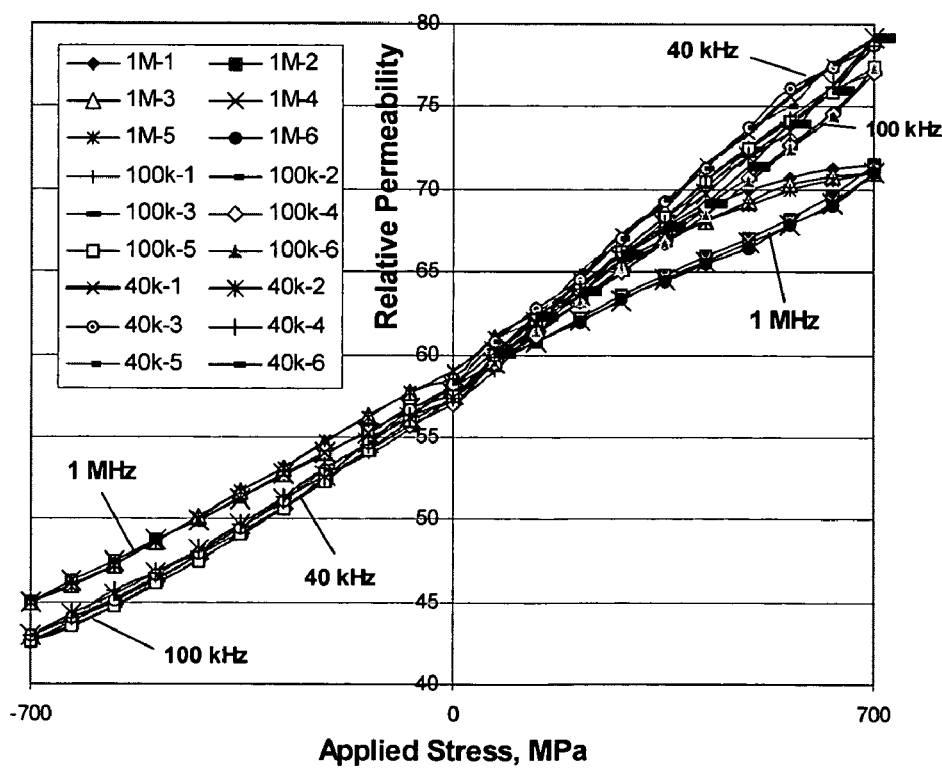
FIG. 22 shows the MWM measured magnetic permeability versus bending stress in a high-strength steel specimen at stresses from −700 to 700 MPa. The specimen was shot peened.

Another example application is stress management during assembly. Fasteners are commonly used to join material layers and considerable effort goes into ensuring that they are tightened to a proper torque setting. Furthermore, manufacturing and cold forming processes commonly result in significant residual stresses that require heat treatment for removal. Mounting of sensors in the vicinity of complex geometries, such as fastener holes, can permit the monitoring of the stresses in the fastener or material layers. FIG. 22 shows a representative image of how the permeability measured at frequencies of 40 kHz, 100 kHz, and 1 MHz changes with applied bending stress. The data illustrate the sensitivity and quality of the permeability measurements for stress measurements in high strength steels over a wide range of stresses. The results clearly show the sensitivity of the MWM measurements to stress changes and reasonably small hysteresis, particularly in the compressive stress range. This capability to perform stress dependent permeability measurements allows is described in now abandoned U.S. patent application Ser. No. 10/441,976, filed May 20, 2003, which published as U.S. Patent Application Publication 2004/0056654, the entire teachings of which are incorporated herein by reference.

Figure 23:
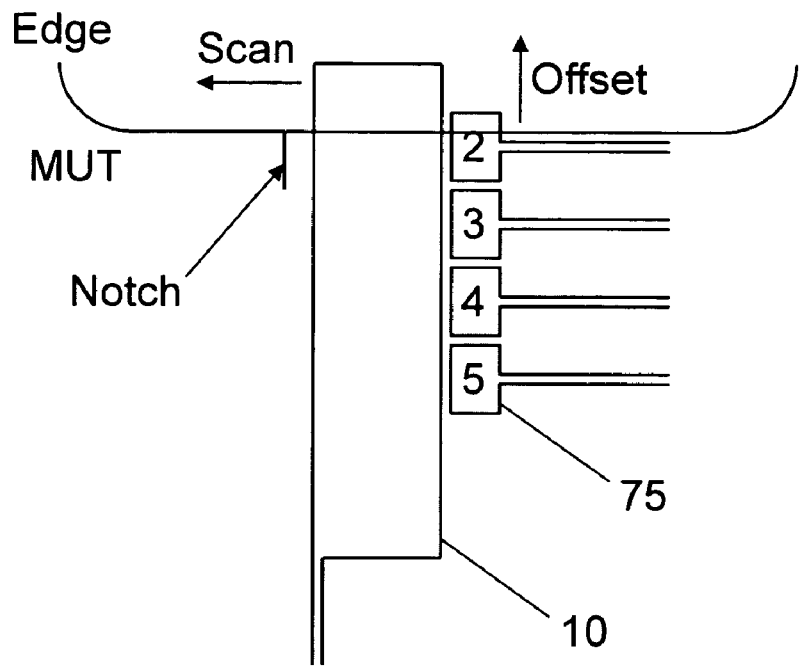
FIG. 23 shows a schematic diagram of an MWM scanned over an edge of a test material.
Figure 24:
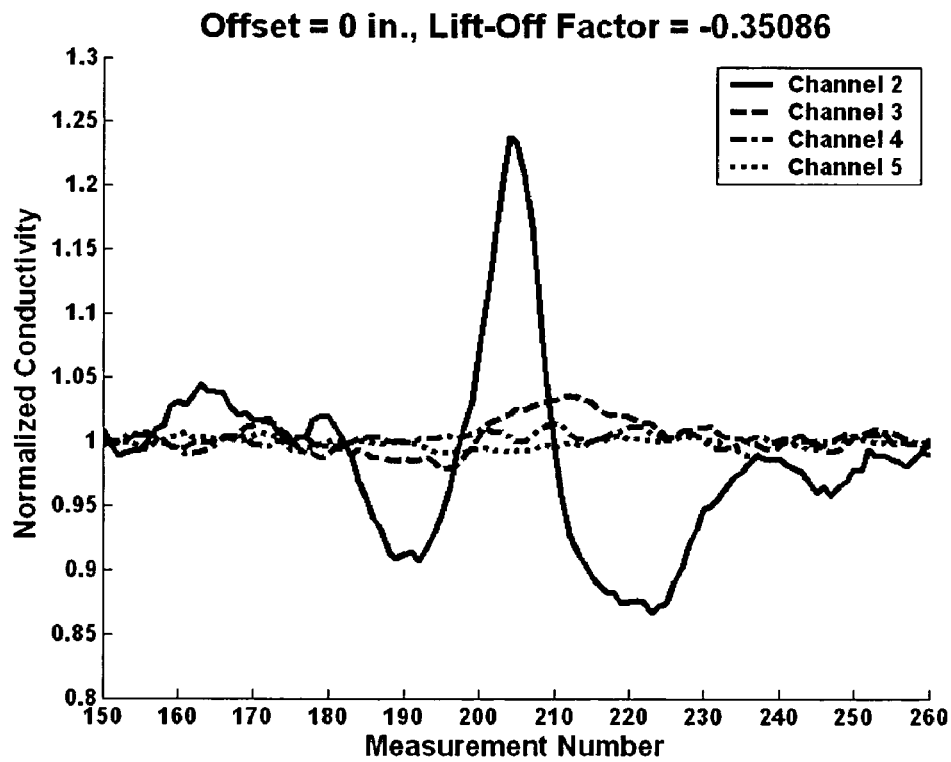
Figure 25:
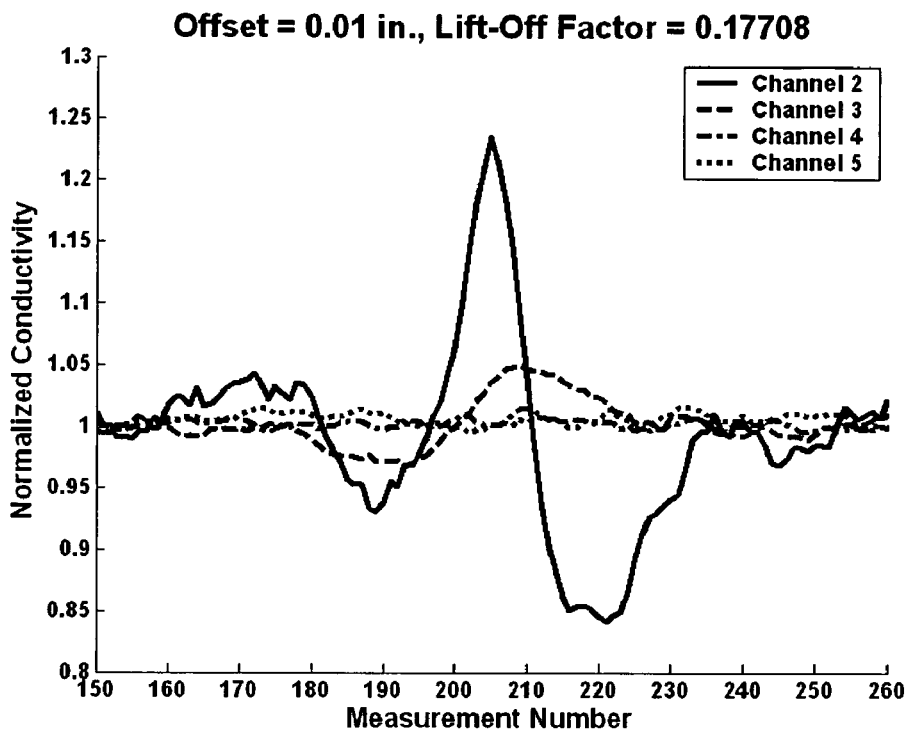
Figure 26:
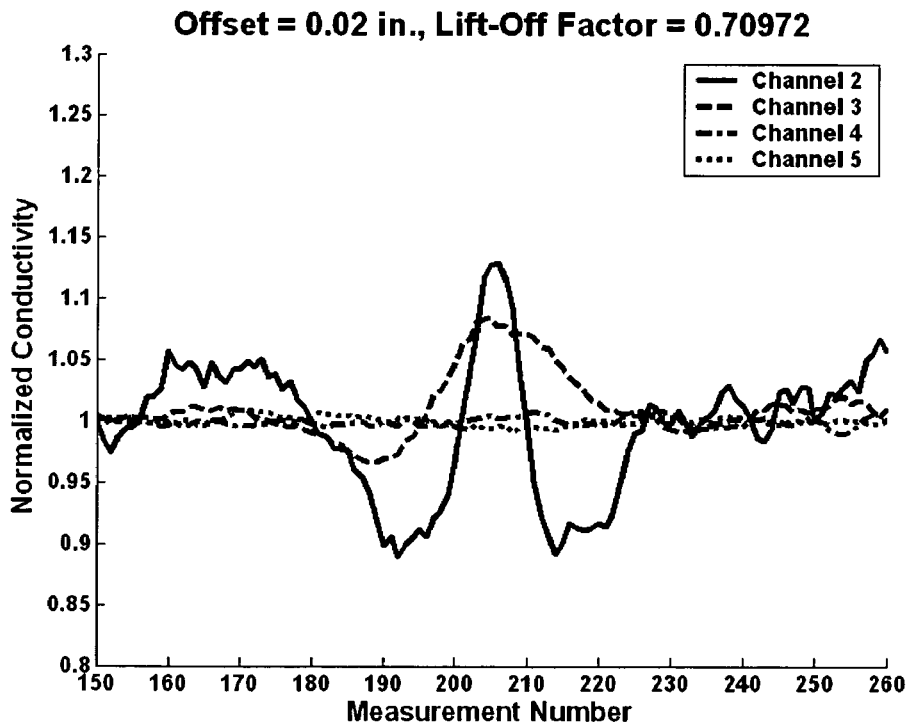
Figure 27:
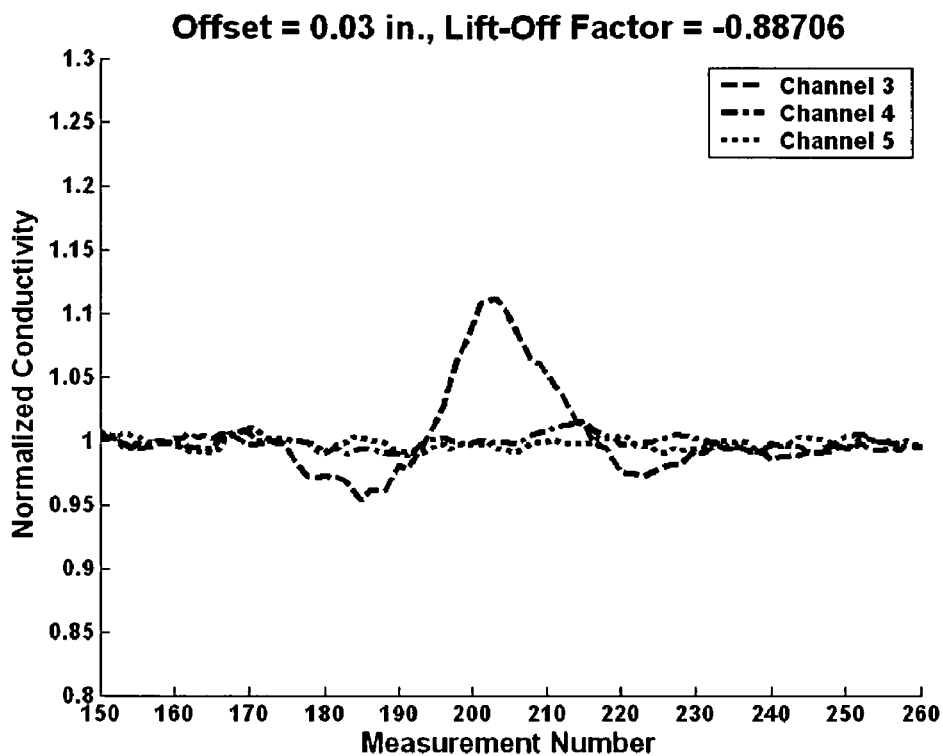
Figure 28:
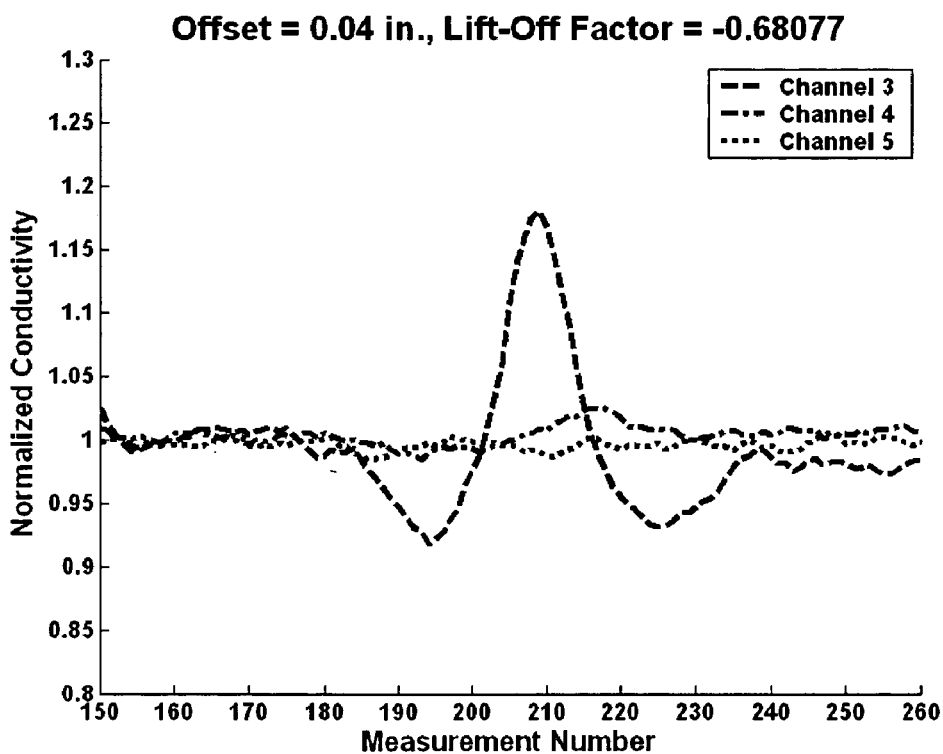
Figure 29:
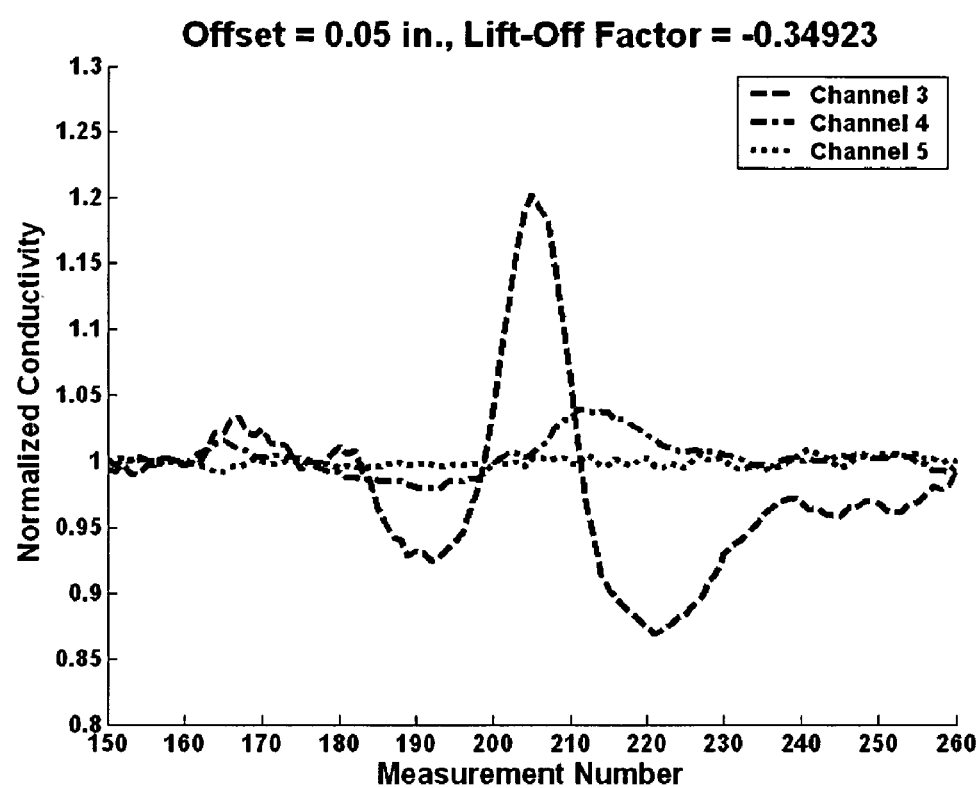

Another desirable attribute for the characterization of local features such as cracks or notches is to be able to compensate or account for deterministic variables in the measurement, such as the location of a sense element over the edge of a test material or even the lift-off variation associated, for example, with varying paint layer thicknesses. This can be achieved by a using measurement information away from the local feature, for example to determine the sensor lift-off, or the response of the sense element itself where part of the sense element is hanging off of the part. One such example is shown in FIG. 23, where a crack is at the edge of the MUT. This configuration is described in expired U.S. Provisional Application No. 60/720,859, filed Sep. 27, 2005, the entire teachings of which are incorporated herein by reference. As the sensor array is scanned along the edge, any misalignment or offset of the sense elements with respect to the edge can change the signature response to the crack (or notch) and limit the sensitivity of the measurement. FIGS. 24-29 show the results of repeatedly scanning a sensor array along the edge of a flat specimen with various offset distances of the sensor array from the edge. Note that the channel numbers in these plots correspond to the sense elements shown in FIG. 23 and the distance between sense element centers is about 0.050 in. In FIG. 24, the offset distance is 0.0 in. and channel 2 is approximately centered over the edge of the test material. As the offset distance increases to 0.01 in. (FIG. 25) and 0.02 in. (FIG. 26), the shape of the crack response changes dramatically. When the offset distance has increased to 0.03 in. (FIG. 27) channel 2 is off of the test material and channel 3 is at the edge of the material. Increasing the offset distance further (e.g., 0.04 in) now causes the crack response curve to change for channel 3. (FIG. 28) When the offset distance is 0.05 in. (FIG. 29) channel 3 is centered over the edge of the material and the crack response is similar to that of channel 2 when the offset distance was 0.0 in. (FIG. 24). This self-similarity of the sense element responses indicates that if the relative position of the sense element or channel from the edge could be determined, then the correct signature could be selected for filtering of the crack response data.

The appropriate signature scan for filtering the response data is determined through a lift-off factor. The lift-off factor is a linear function of the mean effective lift-off h in a short section of the scan preceding the EDM-notch response and defined by $$\text{lift-off factor} = \frac{h - h_o}{a} \quad (37)$$

The constant $h_o$ is chosen so that the lift-off factor is zero for the position of the sensing element relative to the edge that produces the largest EDM-notch response. The constant a is chosen so that the lift-off factor varies from approximately −1 to 1 over the range of positions of a sensing element relative to the edge for which it is the member of the array most sensitive to the EDM-notch. Note that a lift-off factor can be calculated for each sensing element independently. In FIGS. 24-29, the lift-off factor given corresponds to the sensing element which is most sensitive to the EDM-notch.

Note that the procedure for determining the lift-off factor involved performing a series of scans over a notch along the edge of a test material. This allowed a signature response database to be obtained, so that measurements on test parts could use the lift-off factor to determine the appropriate reference scan for filtering of the data. The shape filtering of data is described, for example, in U.S. Pat. No. 6,784,662 and U.S. patent application Ser. No. 10/345,883, filed Jan. 15, 2003, now abandoned, and which published as U.S. Patent Application Publication 2003/0164700, and pending U.S. patent application Ser. No. 11/229,844, filed Sep. 19, 2005, the entire contents of which are incorporated herein by reference. This filtering allows the measurement data to be compared to the reference response to highlight the presence of a crack. Note that the signature responses can be determined empirically or through numerical methods. Furthermore interpolation between reference scans can be used to create the final reference scan compared to the measurement data. This lift-off factor can also be used to correct the response of adjacent sense elements in a sensor array. For example, this reference parameter could be used to select the appropriate response signature for the adjacent element, assuming a notch or crack at the edge, which should provide complementary information about any indicated flaws and may help to reduce the false call rate.

While the inventions have been particularly shown and described with reference to preferred embodiments thereof, it will be understood to those skilled in the art that various changes in form and details may be made therein without departing from the spirit and scope of the invention as defined by the appended claims.

The following references are also incorporated herein by reference in their entirety.

1. Navy Phase II Final Report, titled "*Three Dimensional Magnetic Imaging of Damage in Multiple Layer Aircraft Structure*" Topic #N02-28144, dated Aug. 1, 2005.
2. Strang G., *Introduction to Applied Mathematics*. Wellesley-Cambridge Press, Wellesley, Mass., 1986.

What is claimed is:

1. A method for detecting a local feature in a material comprising:
   providing a database of a plurality of reference responses for a sensor and a feature in a test material, a reference parameter value associated with each reference response;
   disposing a sensor proximate to a test material, the sensor comprising a drive conductor for imposing a field and at least one sense element for sensing the field;
   measuring a sense element response;
   converting the sense element response into a sensed reference parameter value;
   using the sensed reference parameter value to determine a reference response from the database; and
   comparing the measured response and the determined reference response to determine presence of the local feature.

2. A method as claimed in claim 1 wherein the field is a magnetic field.

3. A method as claimed in claim 1 wherein the sensor is disposed near a material edge.

4. A method as claimed in claim 3 wherein the sense element response is measured at multiple positions along the material edge.

5. A method as claimed in claim 1 wherein the sensor is near a material edge and the reference parameter represents sense element position over the edge.

6. A method as claimed in claim 5 wherein the parameter that represents sense element position is a linear function of the lift-off.

7. A method as claimed in claim 1 wherein the response is converted into a lift-off and an effective material property.

8. A method as claimed in claim 7 wherein the reference parameter is lift-off.

9. A method as claimed in claim 7 wherein an effective property is electrical conductivity.

10. A method for detecting a local feature in a material comprising:
disposing a sensor proximate to a test material, the sensor comprising a drive conductor for imposing a field and at least one sense element for sensing the field;
measuring a sense element response;
converting the sense element response into a sensed reference parameter value;
using the sensed reference parameter value to determine a reference response from the database; and
comparing the measured response and the determined reference response to determine presence of the local feature;
the sensor element response being converted into a lift-off and an effective material property.

11. A method as claimed in claim 10 wherein the reference parameter is lift-off.

12. A method as claimed in claim 10 wherein an effective property is electrical conductivity.

13. A method as claimed in claim 10 wherein the sensor is near a material edge and the reference parameter represents sense element position over the edge.

14. A method as claimed in claim 13 wherein the parameter that represents sense element position is a linear function of the lift-off.

* * * * *

UNITED STATES PATENT AND TRADEMARK OFFICE
CERTIFICATE OF CORRECTION

PATENT NO. : 7,289,913 B2
APPLICATION NO. : 11/249047
DATED : October 30, 2007
INVENTOR(S) : Darrell E. Schlicker et al.

It is certified that error appears in the above-identified patent and that said Letters Patent is hereby corrected as shown below:

Column 31

Claim 5, lines 4 through 6, please delete "sensor is near a material edge and the reference parameter represents sense element position over the edge." and insert -- response is converted into a lift-off and an effective material property. --

Claim 6, lines 7 through 9, please delete "parameter that represents sense element position is a linear function of the lift-off." and insert -- reference parameter is lift-off. --

Claim 7, lines through 11, please delete "response is converted into a lift-off and an effective material property." and insert -- sensor is near a material edge and the reference parameter represents sense element position over the edge. --

Claim 8, lines 12 through 13, please delete "reference parameter is lift-off." and insert -- parameter that represents sense element position is a linear function of the lift-off. --

Claim 9, line 14, please delete "7" and insert -- 5 --

UNITED STATES PATENT AND TRADEMARK OFFICE
CERTIFICATE OF CORRECTION

PATENT NO. : 7,289,913 B2
APPLICATION NO. : 11/249047
DATED : October 30, 2007
INVENTOR(S) : Darrell E. Schlicker et al.

It is certified that error appears in the above-identified patent and that said Letters Patent is hereby corrected as shown below:

<u>Column 32</u>

Claim 12, lines 12 through 13, please delete "an effective property is electrical conductivity." and insert -- the sensor is near a material edge and the reference parameter represents sense element position over the edge. --

Claim 13, lines 14 through 16, please delete "10 wherein the sensor is near a material edge and the reference parameter represents sense element position over the edge." and insert -- 12 wherein the parameter that represents sense element position is a linear function of the lift-off. --

Claim 14, lines 17 through 19, please delete "13 wherein the parameter that represents sense element position is a linear function of the lift-off." and insert -- 10 wherein an effective property is electrical conductivity. --

Signed and Sealed this

Eleventh Day of March, 2008

JON W. DUDAS
*Director of the United States Patent and Trademark Office*